(12) United States Patent
Sabatini et al.

(10) Patent No.: US 7,906,308 B2
(45) Date of Patent: Mar. 15, 2011

(54) PHOSPHORYLATION AND REGULATION OF AKT/PKB BY THE RICTOR-MTOR COMPLEX

(75) Inventors: David M. Sabatini, Cambridge, MA (US); Dos D. Sarbassov, Shrewsbury, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 11/341,908

(22) Filed: Jan. 27, 2006

(65) Prior Publication Data

US 2006/0194271 A1  Aug. 31, 2006

Related U.S. Application Data

(60) Provisional application No. 60/648,636, filed on Jan. 28, 2005, provisional application No. 60/654,734, filed on Feb. 18, 2005.

(51) Int. Cl.
*C12N 9/12* (2006.01)
*C12Q 1/00* (2006.01)
*C12P 21/06* (2006.01)
*C12N 15/09* (2006.01)
*C12N 9/00* (2006.01)
*A61K 38/43* (2006.01)
*A61K 39/00* (2006.01)
*A23J 1/00* (2006.01)

(52) U.S. Cl. ......... 435/194; 435/4; 435/69.1; 435/69.2; 435/183; 424/94.1; 424/277.1; 530/412

(58) Field of Classification Search ......................... None
See application file for complete search history.

(56) References Cited

FOREIGN PATENT DOCUMENTS
WO   WO 2004/074448   9/2004

OTHER PUBLICATIONS

Alessi et al., "Characterization of a 3-phosphoinositide-dependent protein kinase which phosphorylates and activates protein kinase Bα," *Curr. Biol.*, 7:261-269 (1997).
Balendran et al., "PDK1 acquires PDK2 activity in the presence of a synthetic peptide derived from the carboxyl terminus of PRK2," *Curr Biol*, 9:393-S3 (1999).
Biondi et al., "The PIF-binding pocket in PDK1 is essential for activation of S6K and SGK, but not PKB," *Embo J.*, 20:4380-4390 (2001).
Brown et al., "A mammalian protein targeted by G1-arresting rapamycin-receptor complex," *Nature* 369:756-758 (1994).
Brunet et al., "Akt Promotes Cell Survival by Phosphorylating and Inhibiting a Forkhead Transcription Factor," *Cell*, 96:857-868 (1999).
Burnett et al., "RAFT1 phosphorylation of the translational regulators of p70 S6 kinase and 4E-BP1," *PNAS*, 95:1432-1437 (1998).

Chen, J., et al., "Identification of an 11-kDa FKBP12-rapamycin-binding domain within the 289-kDa FKBP12-rapamycin-associated protein and characterization of a critical serine residue," Proc. Natl. Acad. Sci. USA, 92:4947-4951 (1995).
Chen et al., "Growth retardation and increased apoptosis in mice with homozygous disruption of the akt1 gene," *Genes Dev.*, 15:2203 (2001).
Chinni and Sarkar, "Akt Inactivation Is a Key Event in Indole-3-carbinol-induced Apoptosis in PC-3 Cells," *Clin. Cancer Res.*, 8:1228-1236 (2002).
Cho et al., "Akt1/PKBα Is Required for Normal Growth but Dispensable for Maintenance of Glucose Homeostasis in Mice," *J. Biol. Chem.*, 276:38349 (2001).
Cho et al., "Insulin Resistance and a Diabetes Mellitus-Like Syndrome in Mice Lacking the Protein Kinase Akt2 (PKBβ)," *Science*, 292:1728 (2001).
Dennis, P.B. et al., "Mammalian TOR: A Homeostatic ATP Sensor," *Science*, 294:1102-1105 (2001).
Edinger et al., "Akt Maintains Cell Size and Survival by Increasing mTOR-Dependent Nutrient Uptake," *Molecular Biology of the Cell*, 13(7):2276-2288 (2002).
Edinger et al., "Differential Effects of Rapamycin on Mammalian Target of Rapamycin Signaling Functions in Mammalian Cells," *Cancer Research*, 63(23):8451-8460 (2003).
Elks and Manganiello, "Antilipolytic Action of Insulin: Role of cAMP Phosphodiesterase Activation," *Endocrinology*, 116:2119-2121 (1985).
Feng et al., "Identification of a PKB/Akt Hydrophobic Motif Ser-473 Kinase as DNA-dependent Protein Kinase," *J. Biol. Chem.*, 279:41189 (2004).
Frost and Lane, "Evidence for the Involvement of Vicinal Sulfhydryl Groups in Insulin-activated Hexose Transport by 3T3-L1 Adipocytes," *J. Biol. Chem.*, 260:2646-2652 (1985).
Gao, X., et al., "Tsc tumour suppressor proteins antagonize amino-acid-TOR signalling," Nature Cell Biology, 4:699-704 (2002).
Guba et al., "Rapamycin inhibits primary and metastatic tumor growth by antiangiogenesis: involvement of vascular endothelial growth factor," *Nat. Med.*, 8:128-135 (2002).
Guertin et al., "An Expanding Role for mTOR in Cancer," *Trends in Molecular Medicine, Elsevier Current Trends*, 11(8):353-361 (2005).
Hara et al., "Raptor, a Binding Partner of Target of Rapamycin (TOR), Mediates TOR Action," Cell, 110:177-189 (2002).
Harrington et al., "The TSC1-2 Tumor suppressor controls insulin-PI3K signaling via regulation of IRS proteins," *J. Cell Biol.*, 166:213-223 (2004).
Hentges et al., "FRAP/mTOR is required for proliferation and patterning during embryonic development in the mouse," PNAS, 98(24):13796-13801 (2001).
Hresko et al., "mTOR Center Dot RICTOR is the Ser(473) Kinase for Akt/Protein Kinase B in 3T3-L1 Adipocytes," *Journal of Biological Chemistry*, 280(49):40406-40416 (2005).
Jacinto et al., "Mammalian TOR Complex 2 Controls the Actin Cytoskeleton and is Rapamycin Insensitive," *Nature Cell Biology*, 6:1122-1128 (2004).
Kane and Weiss, "The PI-3 kinase/Akt pathway and T cell activation: pleiotropic pathways downstream of PIP$_3$," *Immunol. Rev.*, 192:7-20 (2003).
Keith. and Schreiber, Science 270 (5233): 50-1 (abstract).

(Continued)

*Primary Examiner* — Robert M Kelly
*Assistant Examiner* — Kelaginamane Hiriyanna
(74) *Attorney, Agent, or Firm* — Ropes & Gray LLP

(57) ABSTRACT

In certain aspects, the invention relates to methods for identifying compounds which modulate Akt activity mediated by the rictor-mTOR complex and methods for treating or preventing a disorder that is associated with aberrant Akt activity.

6 Claims, 11 Drawing Sheets

OTHER PUBLICATIONS

Kim et al., "mTOR Interacts with Raptor to Form a Nutrient-Sensitive Complex that Signals to the Cell Growth Machinery," Cell, 110(2):163-175 (2002).

Kim et al., "mTOR Interacts with Raptor to Form a Nutrient-Sensitive Complex that Signals to the Cell Growth Machinery," Cell, 110(2):163-175 (2002).

Kops et al., "Directo control of the Forkhead transcription factor AFX by protein kinase B," Nature, 398:630-634 (1999).

Kwiatkowski, D.J., et al., "A mouse model of TSC1 reveals sex-dependent lethality from liver hemangiomas, and up-regulation of p70S6 kinase activity in Tsc1 null cells," Human Molecular Genetics, 11(5):525-534 (2002).

Lawlor et al., "Essential role of PDK1 in regulating cell size and development in mice " Embo J., 21:3728-3738 (2002).

Lee et al., "PTEN Gene Targeting Reveals a Radiation-Induced Size Checkpoint in Human Cancer Cells," Cancer Res., 64:6906-6914 (2004).

Liu et al., "RTG-dependent mitochondria to nucleus signaling is negatively regulated by the seven WD-repeat protein Lst8p" The EMBO Journal, 20(24):7209-7219 (2001).

Loewith et al., "Two TOR Complexes, Only One of which Is Rapamycin Sensitive, Have Distinct Roles in Cell Growth Control," Mol. Cell., 10:457-468 (2002).

Lynch et al. "Integrin-linked kinase regulates phosphorylation of serine 473 of protein kinase B by an indirect mechanism,", Oncogene, 18:8024 (1999).

Mammalian Gene Collection (MGC) Program Team: "Generation and Initial Analysis of More Than 15,000 Full-Length Human and Mouse cDNA Sequences", Proceedings of the National Academy of Sciences of USA, National Academy of Science, 99(26): 16899-16903 (2002).

Morrisett et al., Sirolimus Changes Lipid Concentrations and Lipoprotein Metabolism in Kidney Transplant Recipients, Transplant Proc., 35:143S-150S (2003).

Neshat et al., "Enhanced sensitivity of PTEN-deficient tumors to inhibition of FRAP/mTOR," PNAS, 98(18):10314-10319 (2001).

Nojima et al., "The Mammalian Target of Rapamycin (mTOR) Partner, Raptor, Binds the mTOR Substrates p70 S6 Kinase and 4E-BP1 through Their TOR Signaling (TOS) Motif," Journal of Biological Chemistry, 278(18):15461-15464 (2003).

Ochotorena, I.L., et al., "Conserved Wat1/Pop3 WD-repeat protein of fission yeast secures genome stability through microtubule integrity and may be involved in mRNA maturation," Journal of Cell Science, 114:2911-2920 (2001).

Persad et al., "Regulation of Protein Kinase B/Akt-Serine 473 Phosphorylation by Integrin-linked Kinase," J. Biol. Chem, 276:27462 (2001).

Podsypanina et al., "An inhibitor of mTOR reduces neoplasia and normalizes p70/S6 kinase activity in Pten+/− mice," PNAS, 98(18):10320-10325 (2001).

Radimerski et al., "Lethality of Drosophila lacking TSC tumor suppressor function rescued by reducing dS6K signaling," Genes Dev., 16:2627 (2002).

Rena et al., "Two novel phosphorylation sites on FKHR that are critical for its nuclear exclusion," Embo J., 21:2263-2271 (2002).

Riken Genome Exploration Research Group Phase II Team and Fantom Consortium: "Functional Annotation of a Full-Length Mouse CDNA Collection", Nature, MacMillan Journals Ltd., London, GB, 409(6821): 685-690 (2001).

Roberg, K.J., et al., "Control of Amino Acid Permease Sorting in the Late Secretory Pathway of Saccharomyces cerevisiae by SEC13, LST4, LST7 and LST8," Genetics, 147:1569-1584 (1997).

Rodgers, B.D., et al., "Insulin regulation of a novel WD-40 repeat protein in adipocytes," Journal of Endocrinology, 168:325-332 (2001).

Sabatini, D.M., et al., "RAFT1: A mammalian protein that binds to FKBP12 in a rapamycin-dependent fashion and is homologous to yeast TORs," Cell, 78(1):35-43 (1994).

Sabers et al., "Isolation of a Protein Target of the FKBP12-Rapamycin Complex in Mammalian Cells," J. Biol. Chem., 270:815-822 (1995).

Sarbassov et al., "Growing Roles for the mTOR Pathway," Current Opinion in Cell Biology, Current Science, 17(6):596-603 (2005).

Sarbassov et al., "Phosphorylation and Regulation of Akt/PKB by the Rictor-mTor Complex," Science, 307(5712): 1098-1101 (2005).

Sarbassov et al., "Prolonged Rapamycin Treatment Inhibits mTORC2 Assembly and Akt/PKB," Mol. Cell., 22(2):159-168 (2006).

Sarbassov et al., "Rictor, a Novel Binding Partner of mTor, Defines a Rapamycin-Insensitive and Raptor-Independent Pathway that Regulates the Cytoskeleton," Current Biology,Current Science, 14(14):1296-1302 (2004).

Scheid and Woodgett, "Unraveling the activation mechanisms of protein kinase B/Akt," FEBS Lett., 546:108-112 (2003).

Scheid et al., "Multiple Phosphoinositide 3-Kinase-Dependent Steps in Activation of Protein Kinase B," Mol Cell Biol., 22:6247-6260 (2002).

Schmelzle et al., "TOR, a Central Controller of Cell Growth," Cell, 103(2):253-262 (2000).

Shi et al., "MTOR Inhibitors Activate the AKT Kinase in Multiple Myeloma Cells by Upregulating the IGF-1/IRS-1/PI-3 Kinase Cascade," Blood, 104(11):915A (2004).

Stephens et al., "Protein Kinase B Kinases That Mediate Phosphatidylinositol 3,4,5-Trisphosphate-Dependent Activation of Protein Kinase B," Science, 279:710 (1998).

Taccioli et al., "Targeted Disruption of the Catalytic Subunit of the DNA-PK Gene in Mice Confers Severe Combined Immunodeficiency and Radiosensitivity," Immunity, 9:355 (1998).

Takaishi et al., "Regulation of nuclear translocation of Forkhead transcription factor AFX by protein kinase B," Proc. Natl. Acad. Sci. USA, 96:11836-11841 (1999).

Tang et al., "Negative Regulation of the Forkhead Transcription Factor FKHR by Akt," J. Biol. Chem., 274:16741-16746 (1999).

Toker and Newton, Akt/Protein Kinase B Is Regulated by Autophosphorylation at the Hypothetical PDK-2 Site, J. Biol. Chem., 275:8271 (2000).

Tremblay and Marette, "Amino Acid and Insulin Signaling via the mTOR/p70 S6 Kinase Pathway," J. Biol. Chem., 276:38052-38060 (2001).

Um et al., "Absence of S6K1 protects against age- and diet-induced obesity while enhancing insulin sensitivity," Nature, 431:200-205 (2004).

Vogt, P.K., "PI 3-kinase, mTOR, protein synthesis and cancer," Trends in Molecular Medicine, 7(11):482-484 (2001).

Wijkander et al., "Insulin-Induced Phosphorylation and Activation of Phosphodiesterase 3B in Rat Adipocytes: Possible Role for Protein Kinase B but Not Mitogen-Activated Protein Kinase or p70 S6 Kinase," Endocrinology, 139:219-227 (1998).

Williiams et al., "The role of 3-phosphoinositide-dependent protein kinase 1 in activating AGC kinases defined in embryonic stem cells," Curr Biol., 10:439 (2000).

Xu et al., "The Inducible Expression of the Tumor Suppressor Gene PTEN Promotes Apoptosis and Decreases Cell Size by Inhibiting the PI3K/Akt Pathway in Jurkat T Cells," Cell Growth Differ, 13:285-296 (2002).

Yang et al., "Molecular Mechanism for the Regulation of Protein Kinase B/Akt by Hydrophobic Motif Phosphorylation," Mol. Cell., 9:1227-1240 (2002).

Zhou et al., "Stent Implantation Activates Akt in the Vessel Wall: Role of Mechanical Stretch in Vascular Smooth Muscle Cells," Arterioscler Thromb. Vasc. Biol., 23:2015-2020 (2003).

Alessi et al., "Mechanism of activation of protein kinase B by insulin and IGF-1," Embo J., 15:6541-6551 (1996).

del Peso et al., "Regulation of the forkhead transcription factor FKHR, but not the PAX3-FKHR fusion protein, by the serine/threonine kinase Akt," Oncogene, 18:7328-7333 (1999).

Hill et al., "Insulin-stimulated Protein Kinase B Phosphorylation on Ser-473 Is Independent of Its Activity and Occurs through a Staurosporine-insensitive Kinase," J. Biol. Chem., 276:25643-25646 (2001).

Ohara et al., "Characterization of Size-Fractionated cDNA Libraries Generated by the in vitra Recombination-Assited Method," DNA Research, vol. 9, 47-57 (2002).

| Tissue of Origin/Cancer Type | Cell Line Name | Effect of 24hr rapamycin treatment on Akt/PKB | | | PTEN Status* | Species |
| --- | --- | --- | --- | --- | --- | --- |
| | | Strong Inhibition | Partial Inhibition | None or Increase | | |
| Lymphoma/Leukemia | Jurkat | √ | | | null | human |
| | BJAB | √ | | | null | human |
| | SKW3 | | √ | | | human |
| | U937 | √ | | | null | human |
| | WEHI | | | √ | | mouse |
| | K562 | | | √ | null | human |
| Breast Cancer | MDA-MB-231 | | | √ | | human |
| | MDA-MB-468 | | | √ | null | human |
| Multiple Myeloma | OPM2 | √ | | | null | human |
| | Δ47 | | | √ | null | human |
| Prostate Cancer | PC3 | √ | | | null | human |
| | LNCaP | | | √ | null | human |
| Colorectal Cancer | HT29 | | | √ | | human |
| | CACO2 | | | √ | | human |
| | SW480 | | | √ | | human |
| Endometrial Cancer | Ishikawa | | | √ | null | human |
| Cervical Cancer | HeLa S3 | | | √ | | human |
| | HeLa | | | √ | | human |
| Osteosarcoma | U2OS | | | √ | | human |
| Hepatic Cancer | HepG2 | √ | | | | human |
| Melanoma/Epithelial | UACC-903 | | √ | | null | human |
| | Mel-STRG | | | √ | | human |
| | A375 | | | √ | | human |
| | HMLE | | | √ | | human |
| Rhabdomyosarcoma | Kym-1 | | | √ | | human |
| | Rd88SC.10 | | | √ | | human |
| | rh30 | | | √ | | human |
| Glioblastoma | u87 | | √ | | null | human |
| | 827 | | | √ | null | human |
| Lung Cancer | A549 | | | √ | | human |
| | H460 | | | √ | | human |
| Renal Carcinoma | 786-0 | | | √ | null | human |
| Kidney transformed | HEK-293T | | √ | | | human |
| Fibroblasts | MEFs (p53 -/-) | | √ | | wild-type | mouse |
| | BJ Fibroblasts | | | √ | wild-type | human |
| Skeletal Muscle | c2c12 myoblasts | √ | | | wild-type | mouse |
| Smooth Muscle Cells | rSMC (primary) | | √ | | wild-type | rat |
| Endothelial Cells | HUVEC (primary) | √ | | | wild-type | human |
| Adipocytes | 3t3L1 differentiated | | | √ | wild-type | mouse |

* PTEN status is only noted if evidence is available from the literature. Blank boxes indicate that the status is unknown to us.

PHOSPHORYLATION AND REGULATION OF AKT/PKB BY THE RICTOR-MTOR COMPLEX

RELATED APPLICATIONS

This application claims the benefit of priority of U.S. Provisional Application Nos. 60/648,636 filed Jan. 28, 2005 and 60/654,734 filed Feb. 18, 2005. The teachings of the referenced Provisional Applications are incorporated herein by reference in their entirety.

GOVERNMENT FUNDING

This invention was made with government support under R01 AI47389 awarded by National Institutes of Health. The government has certain rights in the invention.

BACKGROUND OF THE INVENTION

Deregulation of Akt/Protein Kinase B (PKB) is implicated in the pathogenesis of many disorders including cancer and diabetes. Akt/PKB activation requires the phosphorylation of threonine 308 in the activation loop by the phosphoinositide-dependent kinase 1 (PDK1) and serine 473 within the C-terminal hydrophobic motif by an unknown kinase.

The Akt/PKB kinase is a well-characterized effector of phosphoinositide 3-kinase (PI3K) and its deregulation plays important roles in the pathogenesis of human cancers. PI3K is necessary for the activation of Akt/PKB and current models suggest that phosphatidylinositol-3,4,5-triphosphates produced upon growth factor stimulation recruit Akt/PKB to the plasma membrane by binding to its N-terminal pleckstrin homology (PH) domain. At the membrane Akt/PKB is phosphorylated on two key residues: threonine 308 of the activation loop by PDK1 (D. R. Alessi et al., *Curr Biol* 7, 261 (1997); L. Stephens et al., *Science* 279, 710 (1998)), and serine 473 in the hydrophobic motif of the C-terminal tail by a kinase whose identity has been elusive. The role of S473 phosphorylation is controversial, but there is an emerging view that it precedes the phosphorylation of T308 and is important for the recognition and activation of Akt/PKB by PDK1 (M. P. Scheid et al., *Mol Cell Biol* 22, 6247 (2002); J. Yang et al., *Mol Cell* 9, 1227 (2002); D. R. Alessi et al., *Embo J* 15, 6541 (1996)).

SUMMARY OF THE INVENTION

In certain embodiments, the invention provides an isolated, purified or recombinant complex comprising an mTOR polypeptide, a rictor polypeptide, and an Akt polypeptide. Optionally, the subject complex further comprises a GβL polypeptide in addition to the mTOR polypeptide, the rictor polypeptide, and the Akt polypeptide. As described herein, the mTOR polypeptide, the rictor polypeptide, and the Akt polypeptide include the respective wildtype polypeptides, fragments and variants thereof. Preferably, such polypeptides are of eukaryotic origin, such as mammalian origin (e.g., mouse or human).

In certain embodiments, the invention provides a method for inhibiting Akt activity in a cell, comprising contacting the cell with a compound which inhibits function of a rictor-mTOR complex. For example, the compound may inhibit activity or expression of either rictor or mTOR, or both. Alternatively, the compound may inhibit interaction between rictor and mTOR, or interaction between Akt and the rictor-mTOR complex. In certain cases, the compound inhibits assembly of the rictor-mTOR complex. Optionally, the compound inhibits phosphorylation of Akt on S473 by the rictor-mTOR complex. Examples of such compounds include, but are not limited to a peptide, a phosphopeptide, a small organic molecule, an antibody, and a peptidomimetic. Methods of measuring Akt activity are well known in the art, including measuring Akt phosphorylation, Akt kinase activity, and any Akt-mediated signaling (such as regulating cell proliferation, promoting cell survival, and regulating downstream targets such as FKHR). Preferably, the cell is a human cell. In certain cases, the cell is a cancer cell, such as a cancer cell which has no expression or reduced expression of PTEN.

In certain embodiments, the invention provides a method of treating or preventing a disorder that is associated with aberrant Akt activity in a subject, comprising administering to the subject an effective amount of a compound that inhibits function of a rictor-mTOR complex. For example, the disorders associated with aberrant Akt activity include cancer (e.g., a cancer characterized by no expression or reduced expression of PTEN) and diabetes. Preferably, the subject is a human. The compound may inhibit activity or expression of either rictor or mTOR, or both. Alternatively, the compound may inhibit interaction between rictor and mTOR, or interaction between Akt and the rictor-mTOR complex. In certain cases, the compound inhibits assembly of the rictor-mTOR complex. Optionally, the compound inhibits phosphorylation of Akt on S473 by the rictor-mTOR complex. Examples of such compounds include, but are not limited to a peptide, a phosphopeptide, a small organic molecule, an antibody, and a peptidomimetic.

In certain embodiments, the invention provides a method of identifying an antagonist of Akt kinase, comprising: a) contacting a test agent with an Akt polypeptide and a rictor-mTOR complex under conditions appropriate for phosphorylation of Akt by the rictor-mTOR complex; and b) assaying for phosphorylation of Akt by the rictor-mTOR complex in the presence of the test agent, as compared to phosphorylation of Akt by the rictor-mTOR complex in the absence of test agent. If the test agent decreases phosphorylation of Akt by the rictor-mTOR complex, the test agent is an antagonist of Akt kinase. Optionally, the method is conducted in the presence of rapamycin.

Similarly, in certain embodiments, the invention provides a method of identifying an agonist of Akt kinase, comprising: a) contacting a test agent with an Akt polypeptide and a rictor-mTOR complex under conditions appropriate for phosphorylation of Akt by the rictor-mTOR complex; and b) assaying for phosphorylation of Akt by the rictor-mTOR complex in the presence of the test agent, as compared to phosphorylation of Akt by the rictor-mTOR complex in the absence of test agent. If the test agent increases phosphorylation of Akt by the rictor-mTOR complex, the test agent is an agonist of Akt kinase. Optionally, the method is conducted in the presence of rapamycin.

In further embodiments, the invention provides a method of identifying an antitumor agent, comprising: a) contacting a test agent with an Akt polypeptide and a rictor-mTOR complex under conditions appropriate for phosphorylation of Akt by the rictor-mTOR complex; and b) assaying for phosphorylation of Akt by the rictor-mTOR complex in the presence of the test agent, as compared to phosphorylation of Akt by the rictor-mTOR complex in the absence of test agent. If the test agent decreases phosphorylation of Akt by the rictor-mTOR complex, the test agent is an antitumor agent. Optionally, the method is conducted in the presence of rapamycin.

In certain embodiments, the invention provides a method of assessing rapamycin-sensitivity of a cell, comprising: a)

contacting a test cell with rapamycin or a rapamycin analog; and b) assaying for phosphorylation of Akt in the presence of rapamycin or the rapamycin analog, as compared to phosphorylation of Akt in the absence of rapamycin or the rapamycin analog. The test cell is sensitive to rapamycin if rapamycin or the rapamycin analog decreases phosphorylation of Akt. For example, the cell is a cancer cell. Optionally, the cell is a human cell.

In certain embodiments, the invention provides a method of assessing rapamycin-sensitivity of a cell, comprising: a) contacting a test cell with rapamycin or a rapamycin analog; and b) assaying for the amount of rictor-mTOR complex in the presence of rapamycin or the rapamycin analog, as compared to the amount of rictor-mTOR complex in the absence of rapamycin or the rapamycin analog. The test cell is sensitive to rapamycin if rapamycin or the rapamycin analog decreases the amount of rictor-mTOR complex. For example, the cell is a cancer cell. Optionally, the cell is a human cell.

In certain embodiments, the invention provides a method of identifying an agent that enhances rapamycin sensitivity of a cell, comprising: a) contacting a cell with rapamycin or a rapamycin analog; b) contacting a test agent with the cell; b) assaying for the amount of rictor-mTOR complex in the presence of the test agent, as compared to the amount of rictor-mTOR complex in the absence of test agent. The test agent enhances rapamycin sensitivity of the cell if the test agent decreases the amount of rictor-mTOR complex in the cell. For example, the cell is a cancer cell. Optionally, the cell is a human cell.

In certain embodiments, the invention provides a method of enhancing rapamycin sensitivity in a patient, comprising administering to a patient in need thereof a therapeutically effective amount of the agent identified by the present methods. In certain cases, the patient has cancer.

In certain embodiments, the invention provides a method of decreasing an unwanted side effect of rapamycin in a cell, comprising contacting a cell with an agent that enhances Akt activity. For example, the agent increases the amount of rictor-mTOR complex in the presence of rapamycin. To illustrate, the cell is an adipocyte and the unwanted side effect of rapamycin is lipolysis. Optionally, the cell is a human cell.

In certain embodiments, the invention provides a method of decreasing an unwanted side effect of rapamycin in a patient, comprising administering to a patient in need thereof a therapeutically effective amount of the agent that enhances Akt activity. For example, the agent increases the amount of rictor-mTOR complex in the presence of rapamycin. To illustrate, the unwanted side effect of rapamycin is hyperlipidemia. Optionally, the patient is a human.

Figure 8:
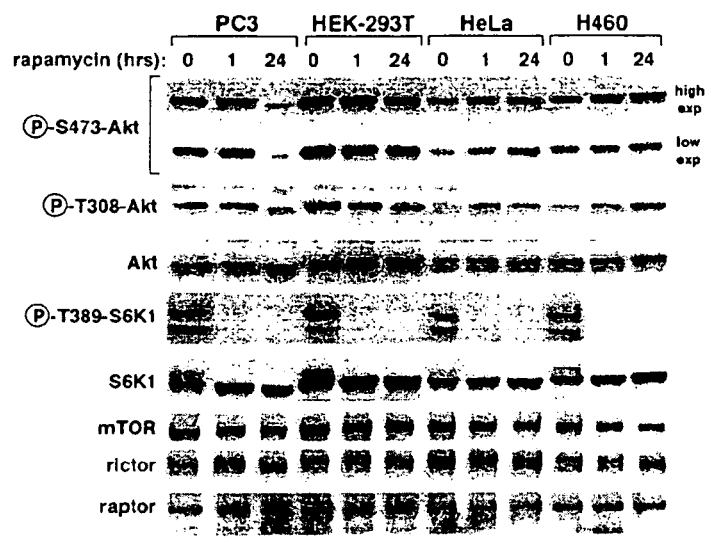
Figure 8:
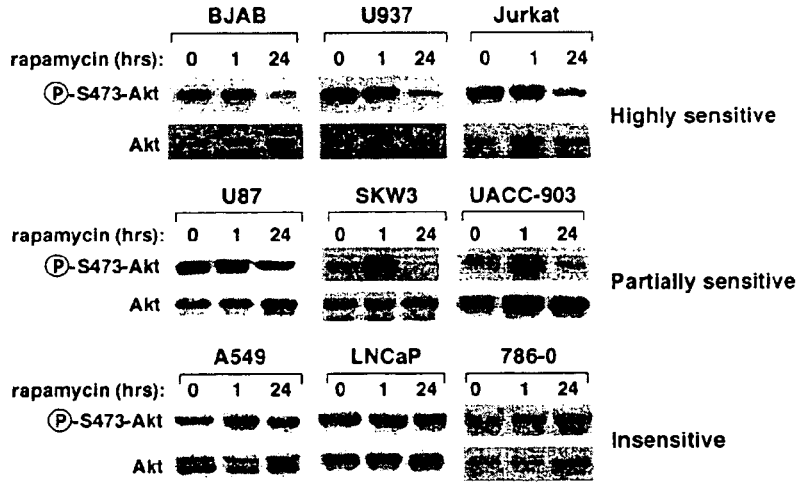
Figure 8:
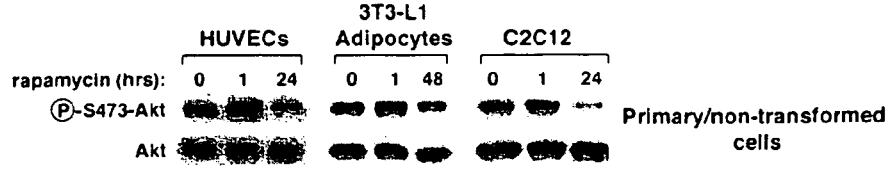

FIGS. 8A-8C show that rapamycin is a cell type-dependent inhibitor of Akt/PKB S473 phosphorylation. (A-C) Indicated cell lines were treated with 100 nM rapamycin for the indicated times and analyzed by immunoblotting for the levels of the indicated proteins and phosphorylation states.

Figure 9:
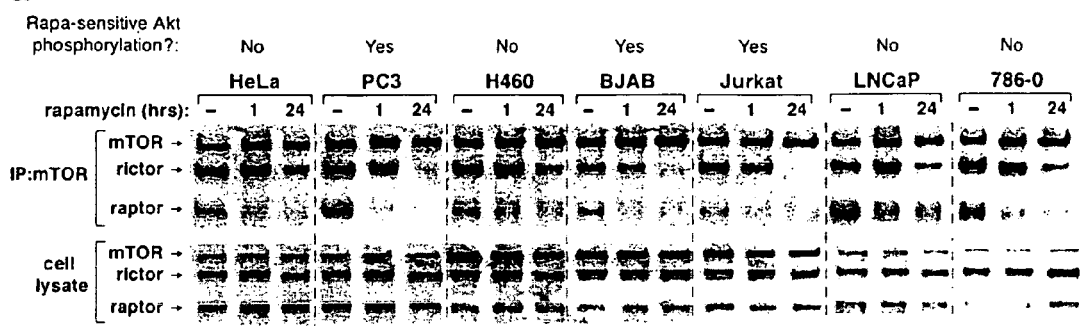
Figure 9:
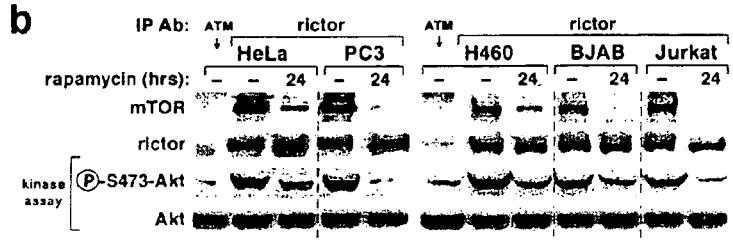
Figure 9:
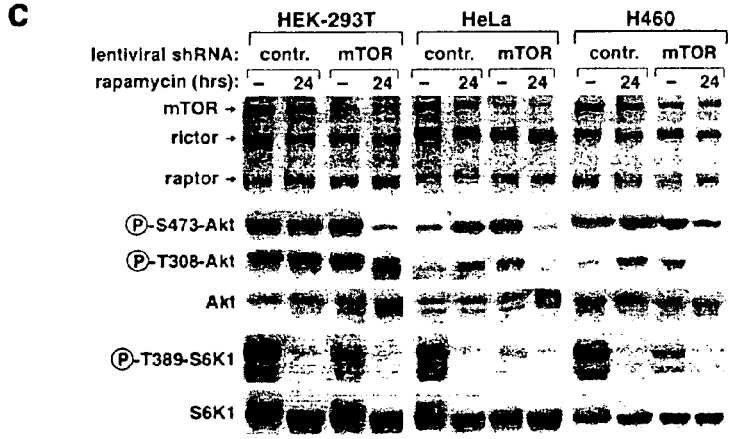

FIGS. 9A-9C show that rapamycin causes an almost complete loss of intact mTORC2 in cell lines with rapamycin-sensitive Akt/PKB phosphorylation. (A) The indicated cells lines were treated with 20 nM rapamycin for 1 or 24 hours. Cell lysates and mTOR-immunoprecipitates prepared from the lysates were analyzed by immunoblotting for levels of mTOR, rictor, and raptor. (B) Rictor immunoprecipitates prepared from cell lines with rapamycin-sensitive Akt/PKB phosphorylation have baseline levels of in vitro kinase activity towards Akt/PKB when isolated from cells treated for 24 hours with rapamycin. Indicated cell lines were treated with or without 100 nM rapamycin for the indicated times and rictor immunoprecipitates prepared from cell lysates were used in kinase assays using Akt1/PKB1 as a substrate as described in the Methods. (C) Partial suppression of mTOR expression converts a cell line with rapamycin-insensitive Akt/PKB phosphorylation to one with rapamycin-sensitive phosphorylation. HEK-293T, HeLa, and H460 cells were infected with lentiviruses expressing a control or mTOR-targeting shRNA and after one day in culture were selected for two additional days with puromycin. Equal cell numbers were then treated with 100 nM rapamycin for the indicated times and mTOR immunoprecipitates and cell lysates analyzed as in FIGS. 7 and 8 for the levels of the indicated proteins and phosphorylation states. The phosphorylation state of S6K1 was used as a marker of the activity of the mTORC 1 pathway. Akt/PKB phosphorylation is less sensitive than S6K1 phosphorylation to a decrease in mTOR expression because a partial loss of mTOR removes the inhibitory signal on PI3K/Akt signaling that is normally mediated by S6K1.

FIGS. 10A-10E show that rapamycin inhibits Akt/PKB signaling and its pro-survival function in vitro and in vivo and these inhibitions require the dephosphorylation of S473. (A) Vector-alone PC3 cells or PC3 cells stably expressing wild-type or S473D Akt1/PKB1 were treated with 100 nM rapamycin for 1 or 24 hours and cell lysates were analyzed by immunoblotting for the indicated proteins and phosphorylation states. Note: exposure times of the Akt/PKB, phospho-S473 Akt/PKB, and phospho-T308 Akt/PKB blots were chosen to show expression levels and phosphorylation states of the recombinant Akt1/PKB1 protein. Also, the S473D Akt1/PKB1 mutant is not recognized by the anti-S473 Akt/PKB antibody. (B) Indicated cell lines were cultured in serum-free medium in the presence of vehicle (DMSO), 100 nM rapamycin (rapa), 100 μM indole-3-carbinol (I3C), or both rapamycin and indole-3-carbinol. After 48 hours the cells were harvested and apoptosis measured by quantifying DNA fragmentation. Results are represented as fold-induction of apoptosis compared to the vector-alone cells grown in the absence rapamycin or indole-3-carbinol. Means±standard deviations for n=3 are shown. (C) Mice with tumor xenografts of vector-alone PC3 cells were treated with rapamycin or vehicle for two days and tumor sections were analyzed with immunohistochemistry for levels of Akt/PKB, phospho-S473 Akt/PKB, and phospho-T308 Akt/PKB. (D) Mice with tumor xenografts made from vector-control PC3 cells or PC3 cells stably expressing wild-type or S473D Akt1/PKB1 were treated with rapamycin or vehicle for two days and tumor sections were analyzed for the presence of apoptotic cells using TUNEL staining (images). Means±standard deviations for n=4 are shown for percentage of apoptotic cells in each tumor type (graph). (E) Mice with tumor xenografts made from the indicated PC3 cell lines were treated with rapamycin or vehicle for two days. Tumor volumes were measured before treatment and at time of tumor harvest. Graph indicates means±standard deviations for percentage change in tumor volume over course of the two-day treatment (n=6 per condition). *=p<0.05 for difference between rapamycin- and vehicle-treated conditions.

Figure 11:
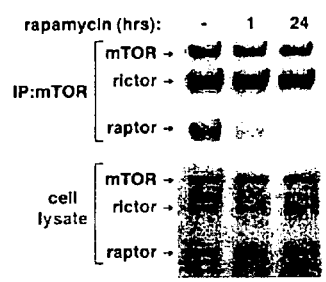

FIG. 11 shows that prolonged in vitro incubation of mTORC1 and mTORC2 with rapamycin leads to disruption of the raptor-mTOR but not rictor-mTOR interaction. A HeLa cell lysate was prepared with a CHAPS-based lysis buffer and divided into three equal portions. One was incubated with 100 nM rapamycin for 1 hour, another with rapamycin for 24 hours, and the third with the drug vehicle for 1 hour. mTOR immunoprecipitates were then prepared and analyzed by immunoblotting for the levels of mTOR, rictor, and raptor.

Figure 12:
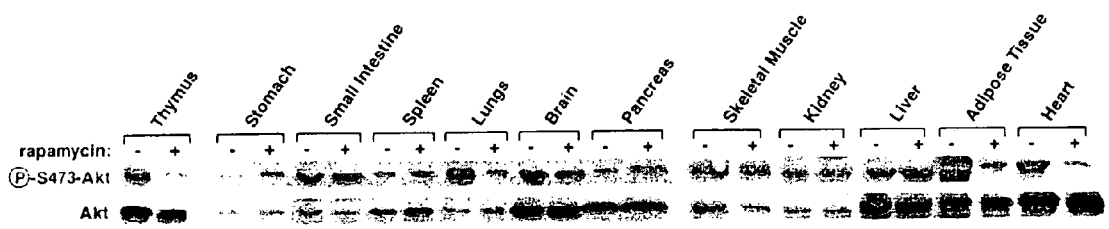

FIG. 12 shows that rapamycin inhibits Akt/PKB phosphorylation in vivo. Mice were treated for one week with daily intraperitoneal injections of rapamycin or the drug vehicle. Tissues were harvested as described in the Methods and Akt/PKB S473 phosphorylation and protein levels were monitored by immunoblotting. Reminiscent of the behavior of several cell lines (FIG. 8), several tissues, notably the stomach and liver, showed rapamycin-induced increases in Akt/PKB phosphorylation.

Figure 13:
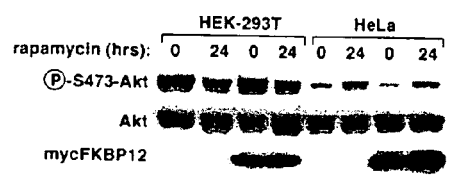

FIG. 13 shows that stable overexpression of FKBP12 does not confer rapamycin-sensitive Akt/PKB phosphorylation. HEK-293T or HeLa cells stably expressing myc-FKBP12 or transduced with the empty vector were treated with 100 nM rapamycin or drug vehicle for 24 hours and analyzed by immunoblotting for the indicated proteins and phosphorylation states.

Figure 14:
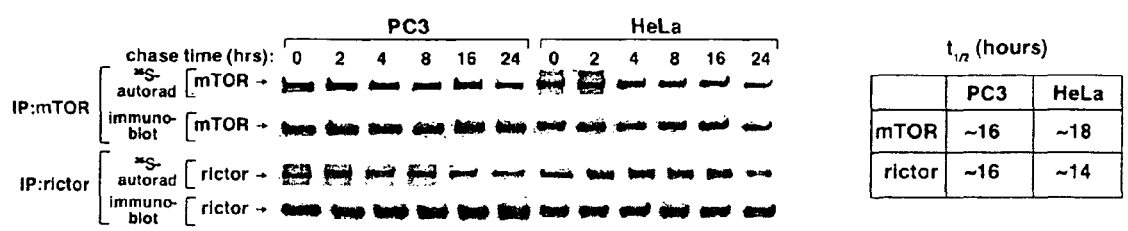

FIG. 14 shows that rictor and mTOR have similar half-lives in both PC3 and HeLa cells. PC3 and HeLa cells were pulse labeled with $^{35}$S-methionine/cysteine and mTOR and rictor were immuoprecipitated at the indicated chase times as described in the Methods. The intensity of the bands corresponding to mTOR and rictor were quantified using a phosphoimager. The rates of disappearance of both proteins were fitted best with linear equations having $R^2$ values ranging from 0.76 to 0.95. These equations were used to calculate half-lives.

FIGS. 15A-15B show that PTEN loss is neither necessary nor sufficient to confer rapamycin-sensitive Akt/PKB phosphorylation to a cell line. (A) PTEN-null Jurkat cells having a doxycycline-inducible PTEN were cultured for 24 hours (left) or one week (right) in the indicated concentrations of doxycyline. The cells were then treated with 100 nM rapamycin for the indicated times and analyzed by immunoblotting for the levels of phospho-S473 Akt/PKB, Akt/PKB, and PTEN. (B) Parental DLD1 cells, DLD1 cells having a stably integrated vector (vector control DLD1), and DLD1 cells null for PTEN were treated with 100 nM rapamycin for the indicated times and analyzed by immunoblotting for the levels of phospho-S473 Akt/PKB, Akt/PKB, and PTEN. DLD1 cells are in the class of cells that increase Akt/PKB phosphorylation with rapamycin treatment.

FIG. 16 shows a survey of 33 cancer/transformed and 6 primary cell lines for rapamycin-sensitivity of Akt/PKB phosphorylation. Cells were treated with 100 nM rapamycin for 24 hours and processed as in FIG. 8. PTEN status was determined from the literature and is indicated only where status is certain. Empty boxes indicate that PTEN status is unknown to us. Using immunoblotting for PTEN Applicants confirmed unpublished references found on the internet that claim that BJAB cells are null for PTEN.

DETAILED DESCRIPTION OF THE INVENTION

The present invention is based, at least in part, on Applicants' discovery that the Target of Rapamycin (TOR) kinase and its associated protein rictor are necessary for S473 phosphorylation of Akt/PKB in eukaryotic cells (e.g., *Drosophila* and human cells) and that prolonged rapamycin treatment inhibits mTORC2 assembly and Akt/PKB.

A reduction in rictor or mTOR expression inhibited Akt/PKB effectors and promoted apoptosis. The rictor-mTOR complex directly phosphorylated Akt/PKB on S473 in vitro and facilitated T308 phosphorylation by PDK1. Rictor-mTOR may serve as a drug target in tumors that have lost the expression of PTEN, a tumor suppressor that opposes Akt/PKB activation. The molecular identity of the S473 kinase (S473K), at times referred to as "PDK2" or the "hydrophobic motif (HM) kinase", has been hotly debated for many years. Several candidate S473 kinases have been proposed, including PDK1 (A. Balendran et al., *Curr Biol* 9, 393 (1999)), Integrin-Linked Kinase (ILK) (S. Persad et al., *J Biol Chem* 276, 27462 (2001)), Akt/PKB itself (A. Toker, A. C. Newton, *J Biol Chem* 275, 8271 (2000)), and, most recently, DNA-$PK_{cs}$ (J. Feng et al., *J Biol Chem* 279, 41189 (2004)). Many lines of evidence argue that neither PDK1, ILK, nor Akt/PKB is the physiological S473 kinase (M. R. Williams et al., *Curr Biol* 10, 439 (2000); D. K. Lynch et al., *Oncogene* 18, 8024 (1999); M. M. Hill et al., *J Biol Chem* 276, 25643 (2001)) and for several reasons DNA-$PK_{cs}$ is also unlikely to have this function. There is no *Drosophila* orthologue of DNA-$PK_{cs}$ (A. S. Dore et al., *DNA Repair (Amst)* 3, 33 (2004)), and, thus, if DNA-$PK_{cs}$ is a physiological S473K in mammals, a distinct kinase must play that role in flies even though all other core components of the pathway (e.g. PI3K, Akt/PKB, PDK1, PTEN) are well conserved. Moreover, it has not been shown that DNA-$PK_{cs}$ phosphorylates full length Akt/PKB, and DNA-$PK_{cs}$ null mice (G. E. Taccioli et al., *Immunity* 9, 355 (1998)) do not suffer the growth retardation or insulin signaling defects associated with Akt1/PKB1 (H. Cho et al., *J Biol Chem* 276, 38349 (2001); W. S. Chen et al., *Genes Dev* 15, 2203 (2001)) or Akt2/PKB2 (H. Cho et al., *Science* 292, 1728 (2001)) null mice, respectively.

Mammalian TOR (mTOR) is a large protein kinase that exists in two distinct complexes within cells: one that contains mTOR, GβL and raptor (D.-H. Kim et al., *Cell* 110, 163 (2002); D.-H. Kim et al., *Molecular Cell* 11, 895 (2003); K. Hara et al., *Cell* 110, 177 (2002); R. Loewith et al., *Mol Cell* 10, 457 (2002)), and another mTOR, GβL and rictor (R. Loewith et al., *Mol Cell* 10, 457 (2002); D. D. Sarbassov et al., *Curr Biol* 14, 1296 (2004)). The raptor-containing complex is sensitive to the drug rapamycin and regulates cell growth, in part by phosphorylating the hydrophobic motif of S6K1 (P. E. Burnett et al., *PNAS* 95, 1432 (1998)), a member of the AGC family of kinases to which Akt/PKB belongs. The rictor-containing complex does not appear to be rapamycin sensitive and its cellular function is just beginning to be understood (D. D. Sarbassov et al., *Curr Biol* 14, 1296 (2004)).

The drug rapamycin has important uses in cardiology, oncology, and transplantation medicine but its clinically relevant molecular effects are not well understood. When bound to FKBP12, rapamycin interacts with and inhibits a multiprotein complex composed of mTOR, mLST8, and raptor (mTORC1). The distinct complex of mTOR, mLST8, and rictor (mTORC2) does not interact with FKBP12-rapamycin and is not thought to be sensitive to rapamycin treatment. mTORC2 phosphorylates and activates the Akt/PKB kinase, a key regulator of cell survival that is hyperactive in cells lacking the PTEN tumor suppressor.

Applicants discovered that prolonged rapamycin treatment of mammalian cells suppresses the assembly of mTORC2. In many, but not all cell types, rapamycin decreases the levels of intact mTORC2 below those needed to maintain Akt/PKB phosphorylation. In such cells, rapamycin inhibits Akt/PKB signaling to the FKHR and AFX transcription factors and potentiates a pro-apoptotic stimulus. These effects are reversed by the expression of an Akt/PKB mutant with a phospho-mimetic residue at the mTORC2 phosphorylation site. In tumors expressing the Akt/PKB mutant the capacity of rapamycin to trigger apoptosis and decrease tumor size is also reduced. Thus, Applicants describe an unforeseen mechanism of action for rapamycin that is cell type dependent and provides a potential molecular explanation for some of the beneficial as well as undesirable clinical effects of the drug. Moreover, Applicants' work indicates that rapamycin, an already clinically approved drug, can be used as an inhibitor of Akt/PKB function in certain tumor cell types.

In certain embodiments, the invention provides an isolated, purified or recombinant complex comprising an mTOR polypeptide, a rictor polypeptide, and an Akt polypeptide. Optionally, the subject complex further comprises a GβL polypeptide in addition to the mTOR polypeptide, the rictor polypeptide, and the Akt polypeptide. As described herein, the mTOR polypeptide, the rictor polypeptide, and the Akt polypeptide include the respective wildtype polypeptides, fragments and variants thereof. Preferably, such polypeptides are of eukaryotic origin, such as mammalian origin (e.g., mouse or human).

In certain embodiments, the invention provides a method for inhibiting Akt activity in a cell, comprising contacting the cell with a compound which inhibits function of a rictor-mTOR complex. For example, the compound may inhibit activity or expression of either rictor or mTOR, or both. Alternatively, the compound may inhibit interaction between rictor and mTOR, or interaction between Akt and the rictor-mTOR complex. Optionally, the compound inhibits phosphorylation of Akt on S473 by the rictor-mTOR complex. Examples of such compounds include, but are not limited to a peptide, a phosphopeptide, a small organic molecule, an antibody, and a peptidomimetic. Methods of measuring Akt activity are well known in the art, including measuring Akt phosphorylation, Akt kinase activity, and any Akt-mediated signaling (such as regulating cell proliferation, promoting cell survival, and regulating downstream targets such as FKHR). Preferably, the cell is a human cell. In certain cases, the cell is a cancer cell, such as a cancer cell which has no expression or reduced expression of PTEN.

In certain embodiments, the invention provides a method of treating or preventing a disorder that is associated with aberrant Akt activity in a subject, comprising administering to the subject an effective amount of a compound that inhibits function of a rictor-mTOR complex. For example, the disorders associated with aberrant Akt activity include cancer (e.g., a cancer characterized by no expression or reduced expression of PTEN) and diabetes. Preferably, the subject is a human. The compound may inhibit activity or expression of either rictor or mTOR, or both. Alternatively, the compound may inhibit interaction between rictor and mTOR, or interaction between Akt and the rictor-mTOR complex. In certain cases, the compound inhibits assembly of the rictor-mTOR complex. Optionally, the compound inhibits phosphorylation of Akt on S473 by the rictor-mTOR complex. Examples of such compounds include, but are not limited to a peptide, a phosphopeptide, a small organic molecule, an antibody, and a peptidomimetic.

In certain embodiments, the invention provides a method of identifying an antagonist of Akt kinase, comprising: a) contacting a test agent with an Akt polypeptide and a rictor-mTOR complex under conditions appropriate for phosphorylation of Akt by the rictor-mTOR complex; and b) assaying for phosphorylation of Akt by the rictor-mTOR complex in the presence of the test agent, as compared to phosphorylation of Akt by the rictor-mTOR complex in the absence of test agent. If the test agent decreases phosphorylation of Akt by the rictor-mTOR complex, the test agent is an antagonist of Akt kinase. Optionally, the method is conducted in the presence of rapamycin.

Similarly, in certain embodiments, the invention provides a method of identifying an agonist of Akt kinase. Such method comprises: a) contacting a test agent with an Akt polypeptide and a rictor-mTOR complex under conditions appropriate for phosphorylation of Akt by the rictor-mTOR complex; and b) assaying for phosphorylation of Akt by the rictor-mTOR complex in the presence of the test agent, as compared to phosphorylation of Akt by the rictor-mTOR complex in the absence of test agent. If the test agent increases phosphorylation of Akt by the rictor-mTOR complex, the test agent is an agonist of Akt kinase. Optionally, the method is conducted in the presence of rapamycin.

In further embodiments, the invention provides a method of identifying an antitumor agent. Such method comprises: a) contacting a test agent with an Akt polypeptide and a rictor-mTOR complex under conditions appropriate for phosphorylation of Akt by the rictor-mTOR complex; and b) assaying for phosphorylation of Akt by the rictor-mTOR complex in the presence of the test agent, as compared to phosphorylation of Akt by the rictor-mTOR complex in the absence of test agent. If the test agent decreases phosphorylation of Akt by the rictor-mTOR complex, the test agent is an antitumor agent. Optionally, the method is conducted in the presence of rapamycin.

In certain aspects, the present invention provides assays for identifying therapeutic agents which either interfere with or promote function of the mTOR-rictor complex. In other aspects, the present invention provides assays for identifying therapeutic agents which modulate (inhibit or enhance) function of Akt. In certain embodiments, an assay of the invention comprises screening for activation of a kinase such as mTOR kinase or Akt. For example, mammalian cells such as HeLa cells are contacted with a compound, and then lysed. mTOR kinase or Akt kinase is then immunoprecipitated and assayed for its activation by methods well known in the art. Optionally, the assays are conducted in the presence of rapamycin.

In certain aspects, agents of the invention may be used to treat certain diseases such as cancer or diabetes, or a disease or condition that is responsive to modulation of the mTOR-rictor complex or Akt. For example, a screening assay of the invention may involve an assay designed to assess the antitumor activity of a test agent. The parameters detected in a screening assay may be compared to a suitable reference. A suitable reference may be an assay run previously, in parallel or later that omits the test agent. A suitable reference may also be an average of previous measurements in the absence of the test agent. In general, the components of a screening assay mixture may be added in any order consistent with the overall activity to be assessed, but certain variations may be preferred. Optionally, in a screening assay, the effect of a test agent may be assessed by, for example, assessing the effect of the test agent on kinetics, steady-state and/or endpoint of the reaction.

Certain embodiments of the invention relate to assays for identifying agents that bind to an mTOR, a rictor, a GβL, or an Akt polypeptide, or a particular domain thereof. A wide variety of assays may be used for this purpose, including labeled in vitro protein-protein binding assays, electrophoretic mobility shift assays, and immunoassays for protein binding. The purified protein may also be used for determination of three-dimensional crystal structure, which can be used for modeling intermolecular interactions and design of test agents. In one embodiment, an assay of the invention detects agents which inhibit interaction between mTOR and rictor. In another example, an assay of the invention detects agents which inhibit interaction between Akt and an mTOR-rictor complex. In certain specific embodiments, the screening methods are conducted in the presence of rapamycin.

In additional embodiments of the invention, assay formats include purified proteins or cell lysates, as well as cell-based assays which utilize intact cells. For example, simple binding assays can be used to detect agents which bind to a rictor, mTOR, Akt, or GβL polypeptide. Such binding assays may also identify agents that act by disrupting the interaction among any two of these polypeptides. Agents to be tested can be produced, for example, by bacteria, yeast or other organisms (e.g., natural products), produced chemically (e.g., small molecules, including peptidomimetics), or produced recombinantly. In one embodiment, the test agent is a small organic molecule having a molecular weight of less than about 2,000 daltons. Assaying rictor-containing complexes (e.g., a complex comprising an mTOR protein and a rictor protein) in the presence and absence of a candidate inhibitor, can be accomplished in any vessel suitable for containing the reactants. Examples include microtitre plates, test tubes, and micro-centrifuge tubes.

Certain embodiments of the invention relate to methods of identifying an agent that enhances rapamycin sensitivity of a cell (e.g., a cancer cell). For example, such methods comprise: a) contacting a cell with rapamycin or a rapamycin analog; b) contacting a test agent with the cell; b) assaying for the amount of rictor-mTOR complex in the presence of the test agent, as compared to the amount of rictor-mTOR complex in the absence of test agent. If the test agent decreases the amount of rictor-mTOR complex in the cell, the test agent is capable of enhancing rapamycin sensitivity of the cell. In other cases, the methods comprise: a) contacting a cell with rapamycin or a rapamycin analog; b) contacting a test agent with the cell; b) assaying for phosphorylation of Akt in the presence of rapamycin or the rapamycin analog, as compared to phosphorylation of Akt in the absence of rapamycin or the rapamycin analog. If the test agent decreases phosphorylation of Akt in the cell, the test agent is capable of enhancing rapamycin sensitivity of the cell. Optionally, the cell is a human cell.

Further embodiments of the invention relate to methods of assessing rapamycin-sensitivity of a cell (e.g., a cancer cell). For example, the methods comprise: a) contacting a test cell with rapamycin or a rapamycin analog; and b) assaying for the amount of rictor-mTOR complex in the presence of rapamycin or the rapamycin analog, as compared to the amount of rictor-mTOR complex in the absence of rapamycin or the rapamycin analog. The test cell is sensitive to rapamycin if rapamycin or the rapamycin analog decreases the amount of rictor-mTOR complex. In other cases, the methods comprise: a) contacting a test cell with rapamycin or a rapamycin analog; and b) assaying for phosphorylation of Akt in the presence of rapamycin or the rapamycin analog, as compared to phosphorylation of Akt in the absence of rapamycin or the rapamycin analog. The test cell is sensitive to rapamycin if rapamycin or the rapamycin analog decreases phosphorylation of Akt. Optionally, the cell is a human cell.

In many drug screening programs which test libraries of compounds and natural extracts, high throughput assays are desirable in order to maximize the number of compounds surveyed in a given period of time. Assays of the present invention which are performed in cell-free systems, such as may be developed with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target.

In certain aspects, the present invention provides a method of treatment for a disease (disorder or condition) affected by aberrant activity of Akt or mTOR-rictor complex, by administering a compound that regulate activity of Akt or mTOR-rictor complex. Any disease that is responsive to Akt or mTOR-rictor complex modulation can be treated by the method of the invention. Examples of such diseases include, but are not limited to, cancer, diabetes, and cardiovascular diseases (e.g., restenosis).

Many diseases or conditions are characterized by or caused by aberrant activation of Akt in an animal. An example of a disease or condition is cancer. Particular examples of cancer include breast cancer, lung cancer, ovarian cancer, endometrial cancer, uterine cancer, brain cancer, sarcoma, melanoma, glioblastoma, leukemia, lymphoma, colorectal cancer, prostate cancer, pancreatic cancer, renal cell cancer, and liver cancer. Another disease or condition is rheumatologic disease, e.g., rheumatoid arthritis or osteoarthritis. A further example of the disease or condition is pulmonary disease, e.g., chronic obstructive pulmonary disease (COPD). The present invention further provides a method of increasing apoptosis of a cell (e.g., a cancer cell), comprising contacting or treating the cell with a compound that is identified by the methods if the present invention.

In certain embodiments, the present invention provides combination or multiple therapies for a condition characterized by or caused by aberrant activation of Akt. For example, the subject methods and compounds may be used in combination with other therapeutic agents, including, but not limited to, anti-cancer agents, antiviral agents, and anti-diabetic agents.

In certain aspects, the present invention provides a method of enhancing rapamycin sensitivity in a patient (e.g., a cancer patient). For example, the method comprises administering to a patient in need thereof a therapeutically effective amount of an agent which decreases phosphorylation of Akt mediated by rictor:mTOR complex or an agent which decreases the amount of rictor:mTOR complex.

In certain aspects, the present invention provides a method of decreasing an unwanted side effect of rapamycin in a patient. For example, the method comprises administering to a patient in need thereof a therapeutically effective amount of the agent that enhances Akt activity in the presence of rapamycin or an agent that enhances assembly of the rictor:mTOR complex in the presence of rapamycin. An example of the unwanted side effect of rapamycin is hyperlipidemia in the patient. Preferably, the patient is a human. In certain specific aspects, the present invention provides a method of decreasing an unwanted side effect of rapamycin in a cell such as an adipocyte. For example, the method comprises contacting a cell with an agent that enhances Akt activity in the presence of rapamycin or an agent that enhances assembly of the rictor:mTOR complex in the presence of rapamycin. An example of the unwanted side effect of rapamycin is lipolysis. Preferably, the cell is a human cell.

When administered to an individual, the compounds of the invention can be administered as a pharmaceutical composition comprising a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of the active therapeutic compound. The physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition.

One skilled in the art would know that a pharmaceutical composition can be administered to a subject by various routes including, for example, oral administration; intramuscular administration; intravenous administration; anal administration; vaginal administration; parenteral administration; nasal administration; intraperitoneal administration; subcutaneous administration and topical administration. The composition can be administered by injection or by incubation. The pharmaceutical composition also can be linked to a liposome or other polymer matrix. Liposomes, for example, which consist of phospholipids or other lipids, are nontoxic, physiologically acceptable and metabolizable carriers that are relatively simple to make and administer.

EXEMPLIFICATION

Example 1

Phosphorylation and Regulation of Akt/PKB by the Rictor-mTOR Complex

Figure 1:
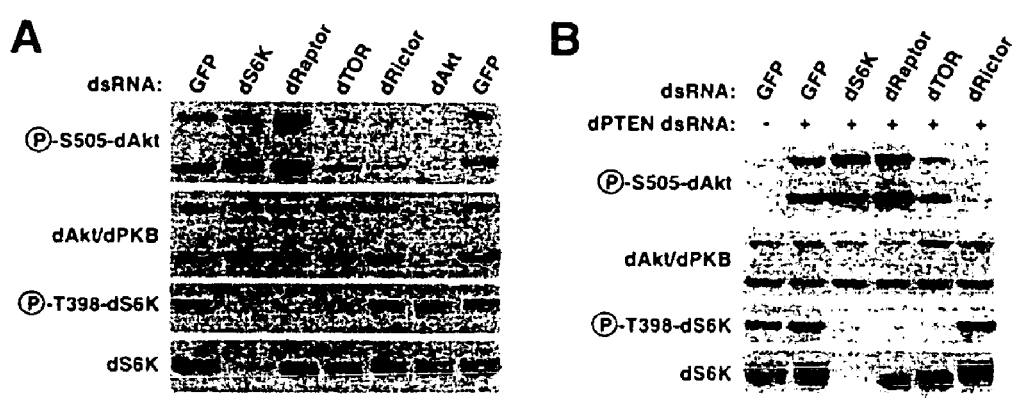
FIGS. 1A-1B show that *Drosophila* rictor and TOR positively regulate the phosphorylation of the hydrophobic motif site of dAkt/dPKB. (A) dsRNAs corresponding to the genes for the indicated proteins were transfected into Kc$_{167}$ *Drosophila* cells. A dsRNA corresponding to Green Fluorescent Protein (GFP) served as a negative control. After 4 days lysates were prepared and analyzed by immunoblotting for levels of phospho- and total dAkt/dPKB and dS6K. (B) dsRNAs corresponding to the genes for the indicated proteins were transfected into Kc167 *Drosophila* cells with (+) or without (−) a dsRNA for dPTEN and samples were analyzed as in (A).

Applicants used RNA interference (RNAi) in cultured *Drosophila* cells to determine the role of TOR pathway components in the phosphorylation of the hydrophobic motif sites of dAkt/dPKB and dS6K. In mammals and *Drosophila*, S6K suppresses signaling through the PI3K/Akt pathway so that inhibition of S6K boosts Akt/PKB phosphorylation (F. Tremblay, A. Marette, *J Biol Chem* 276, 38052 (2001); T. Radimerski et al., *Genes Dev* 16, 2627 (2002); L. S. Harrington et al., *J Cell Biol* 166, 213 (2004)). Knockdown of dS6K or dRaptor expression with double stranded RNAs (dsRNAs) inhibited the phosphorylation and activity of dS6K and increased the phosphorylation of dAkt/dPKB (FIG. 1A). Despite reducing dS6K phosphorylation to the same extent as the dRaptor dsRNA, the dTOR dsRNA failed to increase dAkt/dPKB phosphorylation and, surprisingly, decreased it by a small amount (FIG. 1A). The contrasting effects on dAkt/dPKB phosphorylation by the dTOR and dRaptor dsRNAs suggest that dTOR has an unexpected positive role in dAkt/dPKB signaling that is not shared with dRaptor and that dTOR is required for the increase in dAkt/dPKB phosphorylation caused by dS6K inhibition. Consistent with the dRaptor-independent role for dTOR in dAkt/dPKB phosphorylation, a knockdown of dRictor reduced dAkt/dPKB phosphorylation (FIG. 1A).

Applicants have shown that in *Drosophila* and human cells the Target of Rapamycin (TOR) kinase and its associated protein rictor are necessary for S473 phosphorylation and that a reduction in rictor or mTOR expression inhibited an Akt/PKB effector. The rictor-mTOR complex directly phosphorylated Akt/PKB on S473 in vitro and facilitated T308 phosphorylation by PDK1. Rictor-mTOR may serve as a drug target in tumors that have lost the expression of PTEN, a tumor suppressor that opposes Akt/PKB activation.

Figure 4:
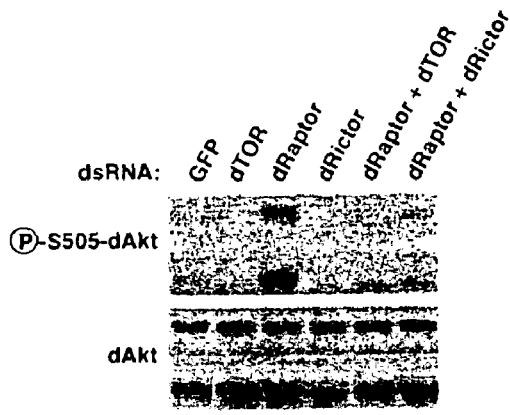
FIG. 4 shows that dRictor and dTOR are required for the increase in dAkt/dPKB phosphorylation caused by a knockdown in dRaptor expression. dsRNAs corresponding to the genes for the indicated proteins were transfected into Kc$_{167}$ *Drosophila* cells. A dsRNA corresponding to Green Fluorescent Protein (GFP) served as a negative control. After 4 days lysates were prepared and analyzed by immunoblotting for levels of phospho- and total dAkt/dPKB.

Because basal dAkt/dPKB phosphorylation is low in *Drosophila* $Kc_{167}$ cells (FIG. 1A), Applicants verified the roles of dRictor and dTOR in cells in which dAkt/dPKB phosphorylation was enhanced by decreasing the expression of dPTEN, the negative regulator of the PI3K/Akt pathway (FIG. 1B). Knockdown of dS6K or dRaptor expression in dPTEN-depleted cells further boosted dAkt/dPKB phosphorylation. In contrast, knockdown of dRictor expression almost completely prevented the dramatic increase in dAkt/dPKB phosphorylation caused by a dPTEN knockdown while the knockdown of dTOR expression caused a slightly smaller suppression (FIG. 1B). dRictor and dTOR were also required for the increase in phosphorylation of dAkt/dPKB caused by a knockdown in the expression of dRaptor (FIG. 4).

Figure 2:
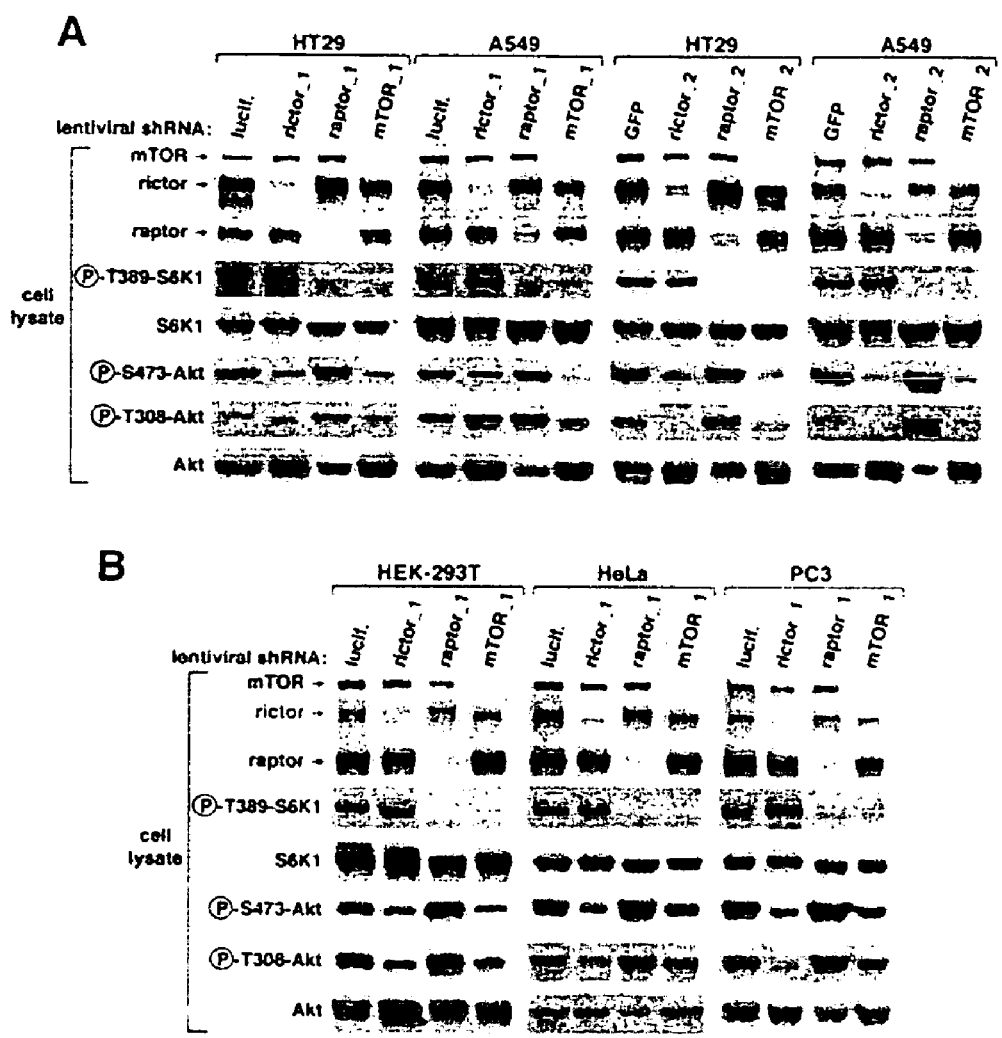
FIGS. 2A-2B show that Rictor and mTOR, but not raptor, positively regulate the phosphorylation of serine 473 and threonine 308 of Akt/PKB in a variety of human cancer cell lines. (A) Immunoblotting was used to analyze the total levels and phosphorylation states of the indicated proteins in two different sets of HT29 and A549 cell lines with stable decreases in rictor, raptor, or mTOR expression. Lentiviruses were used to express control shRNAs targeting luciferase or GFP or shRNAs targeting rictor, raptor, or mTOR (two distinct shRNAs per gene). (B) HEK-293T, HeLa, and PC3 cell lines with stable decreases in rictor, raptor, or mTOR expression were analyzed as in (A).

Results in *Drosophila* cells suggest that dTOR and dRictor have a shared positive role in the phosphorylation of the hydrophobic motif site of dAkt/dPKB. This finding was unexpected because previously (D.-H. Kim et al., *Cell* 110, 163 (2002)). Applicants observed no decrease in the phosphorylation of the hydrophobic motif site of Akt/PKB after reducing mTOR expression in human cells with small interfering RNAs (siRNAs). In retrospect, however, these experiments were undertaken when RNAi-mediated knockdowns of expression in mammalian cells were relatively inefficient. Here, using a lentiviral short hairpin RNA (shRNA) expression system that robustly suppresses gene expression (D. D. Sarbassov et al., *Curr Biol* 14, 1296 (2004)), Applicants obtained results in human cell lines analogous to those in *Drosophila* cells (FIG. 2A). In human HT-29 colon and A549 lung cancer cells, knockdown of rictor or mTOR expression, using two different sets of shRNAs, decreased phosphorylation of both S473 and T308 of Akt/PKB. Mammalian cells may try to compensate for the effects of the rictor and mTOR knockdowns by boosting Akt/PKB expression (FIG. 2A). The decrease in T308 phosphorylation is consistent with the importance of S473 phosphorylation for T308 phosphorylation (M. P. Scheid, P. A. Marignani, J. R. Woodgett, *Mol Cell Biol* 22, 6247 (2002)) and with the fact that the S473D mutant of Akt/PKB is a better substrate than the wild-type protein for T308 phosphorylation by PDK1 (R. M. Biondi, A. Kieloch, R. A. Currie, M. Deak, D. R. Alessi, *Embo J* 20, 4380 (2001)). Knockdown of raptor expression increased the phosphorylation of both S473 and T308 despite reducing Akt/PKB expression. Knockdown of rictor or mTOR expression also decreased S473 phosphorylation in HeLa and HEK-293T cells, two human cell lines that, like A549 and HT-29 cells, contain wild-type PTEN (FIG. 2B). In addition, the knockdowns decreased S473 phosphorylation in the PTEN-null PC-3 prostate cancer cell line (FIG. 2B), a result reminiscent of that in *Drosophila* cells with reduced dPTEN expression (FIG. 1B). Furthermore, the knockdowns decreased S473 phosphorylation in M059J glioblastoma cells that are null for DNA-$PK_{cs}$, a proposed S473K candidate (J. Feng, J. Park, P. Cron, D. Hess, B. A. Hemmings, *J Biol Chem* 279, 41189 (2004)). Thus, in six distinct human cell lines, rictor and mTOR, but not raptor, are necessary for the phosphorylation of the hydrophobic motif of Akt/PKB.

Figure 5:
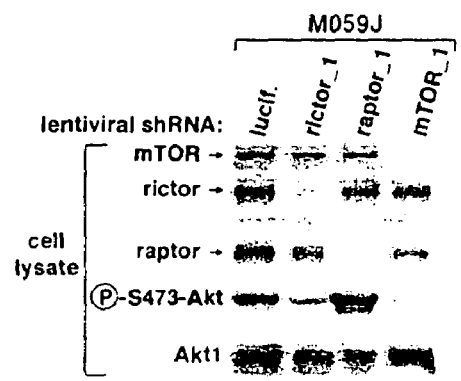
FIG. 5 shows that Rictor and mTOR, but not raptor, positively regulate the phosphorylation of serine 473 of Akt/PKB in a cell line that is null for DNA-P$_{cs}$. Immunoblotting was used to analyze the total levels and phosphorylation states of the indicated proteins in M059J glioblastoma cell lines having stable decreases in rictor, raptor, or mTOR expression. The experiment was analyzed as in FIG. 2.

In a related study, it is shown that Rictor and mTOR, but not raptor, positively regulate the phosphorylation of serine 473 of Akt/PKB in a cell line that is null for DNA-$PK_{cs}$ (FIG. 5). Immunoblotting was used to analyze the total levels and phosphorylation states of the indicated proteins in M059J glioblastoma cell lines having stable decreases in rictor, raptor, or mTOR expression.

Figure 3:
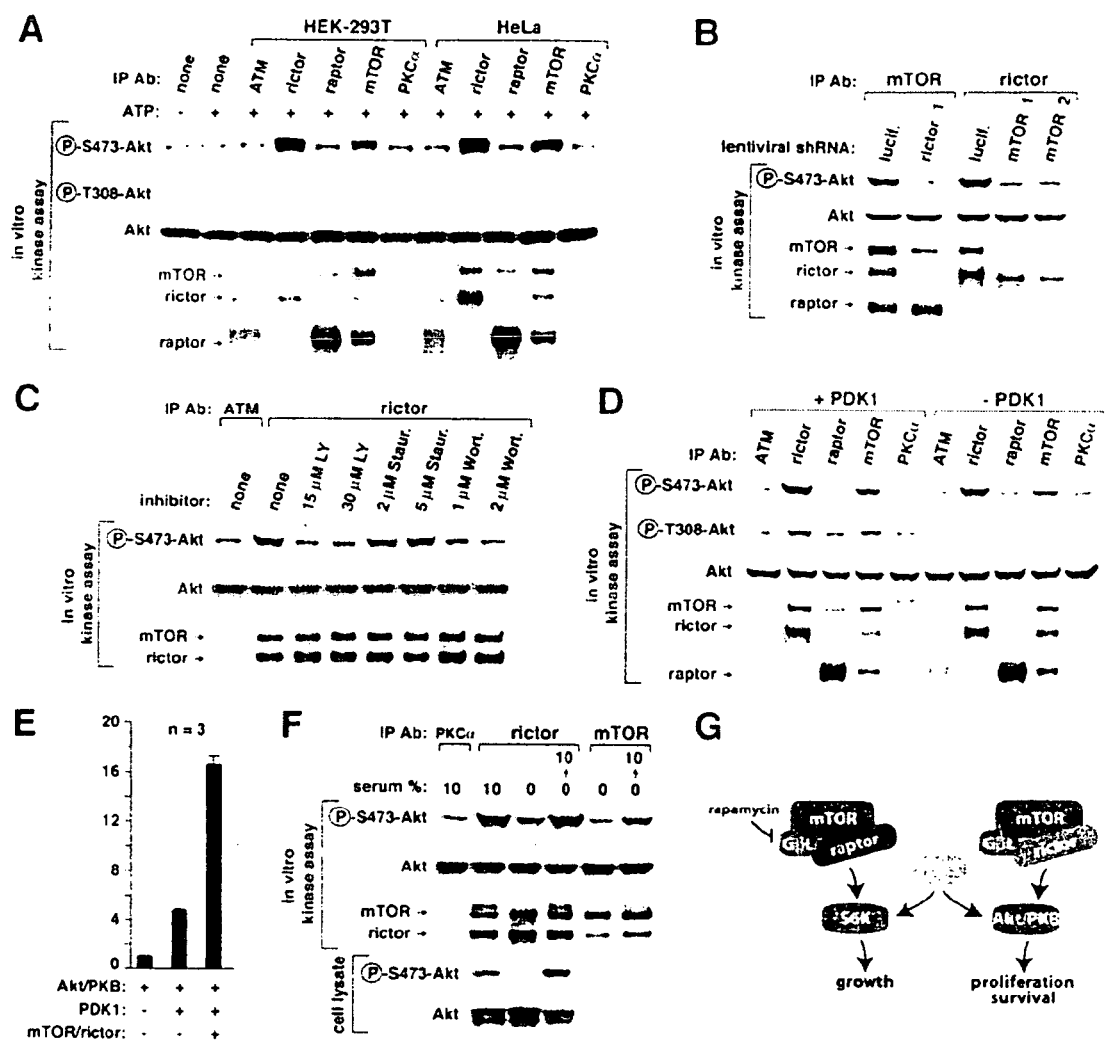
FIGS. 3A-3G show that the rictor-mTOR complex phosphorylates Akt/PKB on S473 in a rictor and mTOR dependent fashion and facilitates phosphorylation of T308 by PDK1. (A) Immunoprecipitates prepared from lysates of HEK-293T or HeLa cells with the indicated antibodies were used in kinase assays with full length, wild-type Akt1/PKB1 as the substrate. Immunoblotting was used to detect the phosphorylation of Akt/PKB at S473 or T308 and the levels of Akt/PKB, rictor, mTOR or raptor in the kinase assays. ATP was omitted from one sample to determine if Akt/PKB authophosphorylation contributes to S473 phosphorylation. (B) Kinase assays were performed as in (A) using cell lines with stable reductions in the expression of rictor (left) or mTOR (right), respectively. (C) Kinase assays containing the indicated concentrations of LY29042 (LY), staurosporine (Staur.), or wortmannin (Wort.) were performed as in (A). (D) The prior phosphorylation of S473 of Akt/PKB by rictor-mTOR increases the subsequent phosphorylation of T308 by PDK1. Assays were performed as in (A) using immunoprecipitates from HeLa cells except that after incubation with the indicated immunoprecipitates 100 ng of PDK1 (+PDK1) was added to half the samples for an additional 20 min incubation. Samples were analyzed with immunoblotting for the indicated phosphorylation states and protein levels. (E) The kinase activity of Akt/PKB after its phosphorylation with PDK1 or with rictor-mTOR followed by PDK1. (F) Kinase assays were performed as in (A) using immunoprecipitates isolated from HeLa cells cultured for 24 hours in media containing 10% or 0% serum, or from serum-deprived cells stimulated with 10% serum for 30 minutes. (G) Schematic diagram of the role of rictor-mTOR in Akt/PKB activation.
Figure 6:
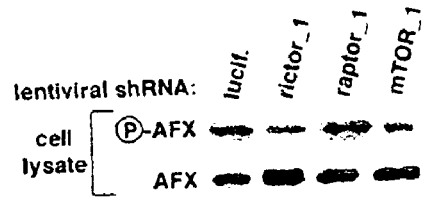
FIG. 6 shows that decreases in rictor or mTOR expression inhibit AFX phosphorylation. Cell lysates from the stable knockdown HeLa cell lines used in FIG. 2B were analyzed by immunoblotting for the phosphorylation states and total levels of the AFX (Foxo4) transcription factors.

As the rictor and mTOR knockdowns inhibit phosphorylation events critical for Akt/PKB activity, they should affect Akt/PKB-regulated processes. In HeLa cells, a reduction in the expression of rictor or mTOR, but not raptor, decreased phosphorylation of FKHR (Foxo1) and AFX (Foxo4a) (FIG. 6), forkhead family transcription factors that are direct substrates of Akt/PKB (G. J. Kops et al., *Nature* 398, 630 (1999)). By regulating downstream targets like FKHR, Akt/PKB is implicated in a variety of cellular processes, including promoting cell survival. To determine if rictor and mTOR expression levels affect cell survival, cells with decreased mTOR or rictor expression were assessed for sensitivity to an apoptotic trigger. After a 24-hour serum deprivation, HeLa cells with reduced mTOR or rictor expression exhibited morphological signs of apoptosis, including blebbing and cell rounding and detachment (FIG. 3BC). These cells also had increased levels of cleaved caspase 3, a molecular marker of apoptosis, and of DNA fragmentation (FIG. 3DE). These findings are consistent with rictor-mTOR having a role in the regulation of Akt/PKB, but rictor-mTOR may also have other targets besides Akt/PKB that are involved in the control of apoptosis.

Because the raptor-mTOR complex directly phosphorylates the hydrophobic motif site of S6K1 (P. E. Burnett et al., *PNAS* 95, 1432 (1998)), Applicants determined if rictor-mTOR has an analogous function for Akt/PKB. Rictor-mTOR complexes isolated from HEK-293T or HeLa phosphorylated S473 but not T308 of full length, wild-type Akt/PKB in vitro (FIG. 3A). Immunoprecipitates of raptor, the ATM protein, or protein kinase C alpha (PKCα did not phosphorylate either site, and Akt/PKB did not autophosphorylate S473 (FIG. 3A). Importantly, the raptor immunoprecipitates also contain mTOR but did not phosphorylate Akt/PKB (FIG. 3A), suggesting that for mTOR to phosphorylate Akt/PKB it must be bound to rictor and that raptor cannot substitute. This lack of phosphorylation holds even in the raptor immunoprecipitates isolated from HEK-293T cells that contain as much mTOR as the rictor immunoprecipitates (FIG. 3A). Consistent with a key role for rictor, mTOR immunoprecipitates prepared from the rictor knockdown cells did not phosphorylate Akt/PKB despite containing a similar amount of mTOR as the controls (FIG. 3B). To verify that mTOR is the S473 kinase in the rictor immunoprecipitates, Applicants prepared immunoprecipitates from control cells or from two different lines of mTOR knockdown cells. Although rictor levels were equivalent in all the immunoprecipitates, only those prepared from cells expressing mTOR phosphorylated Akt/PKB in vitro (FIG. 3B). Both the LY294002 and wortmannin mTOR kinase inhibitors blocked the in vitro phosphorylation of Akt/PKB by rictor-mTOR (FIG. 3C) and LY294002 acted at concentrations that inhibit S473 phosphorylation in cells (M. P. Scheid et al., *Mol Cell Biol* 22, 6247 (2002)). Staurosporine, an inhibitor of Akt/PKB kinase activity (M. M. Hill et al., *J Biol Chem* 276, 25643 (2001)), did not decrease the phosphorylation of Akt/PKB by rictor-mTOR. Thus, in vitro the rictor-mTOR complex phosphorylates S473 of Akt/PKB in a rictor- and mTOR-dependent fashion and with a drug sensitivity profile consistent with mTOR being the phosphorylating kinase.

To determine whether the phosphorylation of Akt/PKB on S473 by rictor-mTOR activates Akt/PKB activity, Applicants first used rictor-mTOR to phosphorylate Akt/PKB on S473 and then added PDK1 to the assay to phosphorylate T308. Prior phosphorylation of Akt/PKB on S473 boosted subsequent phosphorylation by PDK1 of T308 (FIG. 3D), consistent with the importance of S473 phosphorylation for T308 phosphorylation (M. P. Scheid, P. A. Marignani, J. R. Woodgett, *Mol Cell Biol* 22, 6247 (2002); J. Yang et al., *Mol Cell* 9, 1227 (2002)), and with the inhibitory effects of the rictor and mTOR knockdowns on T308 phosphorylation (FIG. 2AB). After phosphorylation with rictor-mTOR and PDK1, Akt1/PKB1 had about 4-5 fold more activity than after phosphorylation with PDK1 alone (FIG. 3E), confirming the important role of S473 in fully activating Akt/PKB. Because growth factors control the phosphorylation of Akt/PKB on S473, Applicants determined if the levels of serum in the cell media regulated the in vitro kinase activity of rictor-mTOR towards Akt/PKB. Rictor-mTOR had decreased activity in HeLa cells deprived of serum and was reactivated by serum stimulation for 30 minutes (FIG. 3F), indicating that modulation of the intrinsic kinase activity of rictor-mTOR may be a mechanism for regulating S473 phosphorylation.

Results presented herein indicate that the rictor-mTOR complex is a hydrophobic motif kinase for Akt/PKB (FIG. 3G). Rictor-TOR has essential roles in Akt/PKB hydrophobic motif site phosphorylation in *Drosophila* and human cells and in vitro phosphorylates full length, wild-type Akt/PKB in a serum-sensitive fashion. No other proposed hydrophobic motif kinase has been shown to fulfill all these criteria. With the advantage of previously unavailable information, described herein, it is possible to identify indications in the literature of the important role of mTOR in Akt/PKB activation. Prolonged, but not acute, treatment of certain human cells with rapamycin partially inhibits Akt/PKB phosphorylation (A. L. Edinger et al., *Cancer Res* 63, 8451 (2003)) and Applicants' findings provide a possible rationale to explain these results. Although rapamycin does not bind to a preformed rictor-mTOR complex (D. D. Sarbassov et al., *Curr Biol* 14, 1296 (2004)), during long-term rapamycin treatment, the drug should eventually sequester all the newly synthesized mTOR molecules within cells. Thus, as the rictor-mTOR complex turns over, rapamycin may interfere with its re-assembly, or over time become part of the new complexes. It is reasonable to expect then that prolonged rapamycin treatment may partially inhibit rictor-mTOR activity, which would explain why rapamycin is particularly effective at suppressing the proliferation of tumor cells with hyperactive Akt/PKB. The PI3K/Akt pathway is frequently deregulated in human cancers that have lost the expression of the PTEN tumor suppressor gene and Applicants' findings suggest that direct inhibitors of mTOR-rictor should strongly suppress Akt/PKB activity. Thus, the rictor-mTOR complex, like its raptor-mTOR sibling, may be a valuable drug target.

Materials and Methods

1. Materials

Reagents were obtained from the following sources: protein G-sepharose from Pierce; ATP-[$\gamma$-$^{32}$P] from NEN; compounds LY294002, wortmannin, and staurosporine were obtained from Calbiochem; DMEM from Life Technologies; mTOR, S6K1, ATM, $\alpha$-tubulin, and PKC$\alpha$ antibodies as well as HRP-labeled anti-mouse, anti-goat, and anti-rabbit secondary antibodies from Santa Cruz Biotechnology; phospho-T389 S6K1, phospho-S473 and phospho-T308 Akt/PKB, Akt/PKB, phospho-S256 FKHR (also recognizes phospho-S193 of AFX), FKHR, AFX, cleaved Caspase 3, phospho-S505 *Drosophila* Akt/PKB, and *Drosophila* Akt/PKB antibodies from Cell Signaling; *Drosophila* S6K antibody from Mary Stewart, North Dakota State University; and the rictor and raptor antibodies were previously described (D. D. Sarbassov et al., *Curr Biol* 14, 1296 (2004)). The Cell Death Detection Elisa Plus kit (Roche, # 1774425) was used as described by the manufacturer to quantify DNA fragmentation during apoptosis. All cell lines were obtained from ATCC.

2. Cell Lysis

Cells growing in 10 cm dishes were rinsed once with cold PBS and lysed on ice for 20 min in 1 ml of ice-cold Lysis Buffer (40 mM Hepes pH 7.5, 120 mM NaCl, 1 mM EDTA, 10 mM pyrophosphate, 10 mM glycerophosphate, 50 mM NaF, 0.5 mM orthovanadate, and EDTA-free protease inhibitors (Roche)) containing 1% Triton X-100. After clearing of Triton X-100 material by centrifugation at 13,000×g for 10 min, samples containing 50-100 µg of protein were resolved by SDS-PAGE and proteins transferred to PVDF and visualized by immunoblotting as described (D.-H. Kim et al., *Cell* 110, 163 (2002)). For experiments with FKHR and AFX the Triton X-100 insoluble materials were solubilized in 1% SDS in 10 mM Tris-HCl pH 7.4 by heating at 100° C. for 3 minutes followed by a brief sonication. Equal protein amounts were then analyzed by immunoblotting.

3. Immunoprecipitations and Kinase Assays

For all immunoprecipitation experiments the lysis buffer contained 0.3% CHAPS instead of 1% Triton in order to preserve the integrity of the mTOR complexes (D. D. Sarbassov et al., *Curr Biol* 14, 1296 (2004); D.-H. Kim et al., *Cell* 110, 163 (2002)). 4 µg of the indicated antibodies were added to the cleared cellular lysates and incubated with rotation for 90-min. 25 µl of a 50% slurry of protein G-sepharose was then added and the incubation continued for 1 h. Immunoprecipitates captured with protein G-sepharose were washed four times with the CHAPS Lysis Buffer and once with the rictor-mTOR kinase buffer (25 mM Hepes pH 7.5, 100 mM potassium acetate, 1 mM MgCl$_2$). For kinase reaction immunoprecipitates were incubated in a final volume of 15 µl for 20 min at 37° C. in the rictor-mTOR kinase buffer containing 500 ng inactive Akt1/PKB1 (Ak1t/PKB1, Upstate Biotechnology, #14-279) and 500 µM ATP. The reaction was stopped by the addition of 200 µl ice-cold Enzyme Dilution buffer (20 mM MOPS, pH 7.0, 1 mM EDTA, 0.01% Brij 35, 5% glycerol, 0.1% 2-mercaptoethanol, 1 mg/ml BSA). After a quick spin, the supernatant was removed from the protein G-sepharose and analyzed by immunoblotting (D.-H. Kim et al., *Cell* 110, 163 (2002)). For experiments involving PDK1, the rictor-mTOR phosphorylation was performed as described above and the second reaction was initiated by adding to the samples 100 ng of PDK1 (Upstate Biotechnology, #14-452) and 5 µl of Mg/ATP Cocktail (220 mM MOPS, pH-7.2, 75 mM $MgCl_2$, 500 µM ATP, 25 mM #-glycerol phosphate, 5 mM EGTA, 1 mM sodium orthovanadate, 1 mM DTT; Upstate Biotechnology, #20-113). The samples were incubated for a further 20 min at 37° C., the reactions stopped by adding 40 µl Enzyme Dilution buffer and the samples quickly spun to pellet the protein G-sepharose. Supernatants were used in the Akt1/PKB1 kinase assay as described below and were also analyzed by immunoblotting. The pelleted G-sepharose beads were also analyzed by immunoblotting to determine the levels of rictor, mTOR, and raptor in the immunoprecipitates. Akt1/PKB1 kinase activity was determined using Crosstide (Upstate Biotechnology, #12-331) as substrate as recommended by the manufacturers protocol. Briefly, supernatant samples containing phosphorylated Akt1/PKB1 were incubated for 10 min at 30° C. in a final volume of 25 µl of Akt/PKB kinase buffer (8 mM MOPS pH 7.0, 0.2 mM EDTA) containing 2.5 µl of Crosstide peptide (30 µM final concentration), 4.5 µl of Mg/ATP Cocktail, and 10 µCi of [$\gamma$-$^{32}$P] ATP. After the incubation the samples were cooled on ice and 20 µl aliquots were transferred onto the center of P81 paper square (Upstate Biotechnology, #20-134). After drying the P81 paper squares were washed 3 times for 5 min each time with 0.75% phosphoric acid and once for 5 min with acetone. After the washing, the P81 squares were dried and radioactivity read in a scintillation counter.

4. *Drosophila* RNAi and Analysis dsRNAs targeting *Drosophila* TOR pathway components were synthesized by in vitro transcription in 20 µl reactions using a T7 MEGAscript™ kit (Ambion). DNA templates for IVT were generated by RT-PCR from total *Drosophila* cellular RNA using the OneStep RT-PCR kit (Qiagen). Primers (which incorporated a 5' and 3' T7 promoter) for dAkt and dPTEN dsRNA synthesis were as follows:

```
dPTEN forward primer:
5'GAATTAATACGACTCACTATAGGGAGATTAAGCTATTGGAAGAGAATC
ATGC (SEQ ID NO: 1).

dPTEN reverse primer:
5'GAATTAATACGACTCACTATAGGGAGAATCGATTTCTGATTTGCTTAA
AGTG (SEQ ID NO: 2).

dAkt/dPKB forward primer:
5'GAATTAATACGACTCACTATAGGGAGAGTCAATAAACACAACTTTCGA
CCT (SEQ ID NO: 3).

dAkt/dPKB reverse primer:
5'GAATTAATACGACTCACTATAGGGAGAGAATATTTGAGTGAAATGAGG
AACG (SEQ ID NO: 4).
```

The underlined region indicates the T7 promoter sequence. Primers for the synthesis of other dsRNAs were previously described (D. D. Sarbassov et al., *Curr Biol* 14, 1296 (2004)). dsRNA products were purified by adding 80 µl of RNAse free water to IVT reactions and filter purified with a vacuum manifold using Millipore filter plates (MANU 030 PCR). Final dsRNA concentrations were measured on a Nano-drop spectrophotometer.

*Drosophila* $Kc_{167}$ cells were prepared for dsRNA addition by diluting an overnight culture seeded at $80 \times 10^6$ total cells in 12 ml *Drosophila* Schneider's medium to $1 \times 10^6$ cells/ml in Schneider's. 2 ml of media containing cells was then seeded to each well in 6-well culture dishes. dsRNAs were administered to cells using FuGENE 6 transfection reagent (Roche). Briefly, 3 µl of FuGENE was added to 97 µl of *Drosophila* SFM (Invitrogen), followed by addition of 2 µg of the indicated dsRNA in a sterile eppendorf tube. Tubes were gently mixed and incubated for 15 minutes at room temperature. FuGENE:dsRNA complexes were then administered to cells by adding the entire mix drop-wise around wells and then swirling to ensure even dispersal. For combination dsRNA addition experiments, 1.0 µg of PTEN dsRNA was mixed with 1.0 µg of the indicated dsRNA species (except in the GFP only control which contained 2.0 µg of the GFP dsRNA). Additional FuGENE:dsRNA complexes were added to wells on each of the following 2 days. On the third day of dsRNA addition, the medium was changed to avoid potential negative effects of excessive FuGENE on cell viability. After 4 days total of incubation to allow turnover of the target mRNAs, cell lysates were prepared as described (D. D. Sarbassov et al., *Curr Biol* 14, 1296 (2004)). 50 µg of total cellular protein was loaded per lane on 8% SDS-PAGE gels, separated, transferred to nitrocellulose membranes and analyzed by immunoblotting.

5. Lentiviral shRNA Cloning, Production, and Infection

Desalted oligonucleotides (IDT) were cloned into LKO.1 (S. A. Stewart et al., *RNA* 9, 493 (2003)) with the Age I/EcoRI sites at the 3' end of the human U6 promoter. The sequences of the oligonucleotides are as follows:

```
mTOR_shRNA_1 sense:
5'CCGGCCGCATTGTCTCTATCAAGTTCTTCCTGTCAAACTTGATAGAGA
CAATGCGGTTTTTG (SEQ ID NO: 5)

mTOR_shRNA_1 antisense:
5'AATTCAAAAACCGCATTGTCTCTATCAAGTTTGACAGGAAGAACTTGA
TAGAGACAATGCGG (SEQ ID NO: 6)

Raptor_sRNA_1 sense:
5'CCGGGGCTAGTCTGTTTCGAAATTTCTTCCTGTCAAAATTTCGAAACA
GACTAGCCTTTTTG (SEQ ID NO: 7)

Raptor_sRNA_1 antisense:
5'AATTCAAAAAGGCTAGTCTGTTTCGAAATTTTGACAGGAAGAAATTTC
GAAACAGACTAGCC (SEQ ID NO: 8)

Rictor_sRNA_1 sense:
5'CGGGCAGCCTTGAACTGTTTAACTTCCTgTCATT AAACAGTTCAAGG
CTGCTTTTTG (SEQ ID NO: 9)

Rictor_sRNA_1 antisense:
5'AATTCAAAAAGCAGCCTTGAACTGTTTAATGACAGGAAGTTAAACAGT
TCAAGGCTGC (SEQ ID NO: 10)

mTOR_shRNA_2 sense:
CCGGTTCAGCGTCCCTACCTTCTTCTCTCGAGAGAAGAAGGTAGGGACGC
TGATTTTTG (SEQ ID NO: 11)

mTOR_shRNA_2 antisense:
AATTCAAAAATCAGCGTCCCTACCTTCTTCTCTCGAGAGAAGAAGGTAGG
GACGCTGAA (SEQ ID NO: 12)

Raptor_shRNA_2 sense:
CCGGAGGGCCCTGCTACTCGCTTTTCTCGAGAAAAGCGAGTAGCAGGGCC
CTTTTTTG (SEQ ID NO: 13)

Raptor_sRNA_2 antisense:
AATTCAAAAAAGGGCCCTGCTACTCGCTTTTCTCGAGAAAAGCGAGTAGC
AGGGCCC (SEQ ID NO: 14)

Rictor_sRNA_2 sense:
CCGGTACTTGTGAAGAATCGTATCTTCTCGAGAAGATACGATTCTTCACA
AGTTTTTTG (SEQ ID NO: 15)

Rictor_sRNA_2 antisense:
AATTCAAAAAACTTGTGAAGAATCGTATCTTCTCGAGAAGATACGATTCT
TCACAAGTA (SEQ ID NO: 16)
```

Plasmids were propagated in and purified from Stbl2 bacterial cells (Invitrogen) and co-transfected together with the Delta VPR and CMV VSVG plasmids into actively growing HEK-293T using FuGENE (Roche) as described (D. D. Sarbassov et al., *Curr Biol* 14, 1296 (2004); S. A. Stewart et al., *RNA* 9, 493 (2003)). Virus-containing supernatants were collected at 36 and 60 hours after transfection, and concentrated by ultracentrifugation for 1.5 hrs at 23,000 RPM in an SW28 rotor at 4° C. Pellets were resuspended overnight at 4° C. in 1/600 of the original volume. Cells were infected twice in the presence of 6 µg/ml protamine sulfate, selected for puromycin resistance and analyzed on the 7$^{th}$ day after infection. In previous work, Applicants noted that an acute knockdown of mTOR expression in HEK-293T cells using siRNAs also partially decreased raptor expression (D.-H. Kim et al., *Cell* 110, 163 (2002)). This effect is decreased in magnitude in the chronic mTOR knockdown cell lines made with lentivirally-expressed shRNAs.

Example 2

Prolonged Rapamycin Treatment Inhibits mTORC2 Assembly and Akt/PKB

The mammalian TOR (mTOR) protein nucleates two distinct multiprotein complexes that regulate different pathways (reviewed in Guertin, D. A. & Sabatini, D. M. *Trends Mol Med* 11, 353-61 (2005)). The mTOR complex 1 (mTORC1) consists of mTOR, raptor, and mLST8 (also known as GβL) and regulates cell growth through effectors such as S6K1. The mTOR complex 2 (mTORC2) contains mTOR, rictor, and mLST8 and recent work shows that it regulates Akt/PKB by phosphorylating it on S473 (Sarbassov, D. D. et al. *Science* 307, 1098-101 (2005); Hresko, R. C. & Mueckler, M. *J Biol Chem* (2005)). Together with the phosphorylation of T308 by PDK1, S473 phosphorylation is necessary for full Akt/PKB activation (Alessi, D. R. et al. *Embo J* 15, 6541-51 (1996)). FKBP12-rapamycin binds only to mTORC1, leading to the assumption that the drug exerts its clinical effects by specifically perturbing this complex and its downstream signaling pathway. Although FKBP12-rapamycin cannot bind to pre-formed mTORC2 (Sarbassov, D. D. et al. *Curr Biol* 14, 1296-302 (2004); Jacinto, E. et al. *Nat Cell Biol* 6, 1122-8 (2004)), it does bind to free mTOR (Brown, E. J. et al. *Nature* 369, 756-758 (1994); Sabatini, D. M. et al. *Cell* 78, 35-43 (1994); Sabers, C. J. et al. *J. Biol. Chem.* 270, 815-822 (1995)). Because mTOR molecules should be free when newly synthesized and when mTOR complexes turn over, long term exposure of cells to rapamycin should lead to the binding of FKBP12-rapamycin to a large fraction of the mTOR molecules within cells. As the binding of FKBP12-rapamycin to free mTOR may prevent the subsequent binding of rictor, Applicants hypothesized (Sarbassov, D. D. et al. *Science* 307, 1098-101 (2005)) that prolonged rapamycin treatment may inhibit Akt/PKB signaling by interfering with the assembly of mTORC2.

To determine if rapamycin can alter the levels of intact mTORC2, Applicants treated HeLa or PC3 cells with 100 nM rapamycin for 0.5, 1, 2, or 24 hours and compared the amounts of rictor and raptor bound to mTOR. Rapamycin had little effect on the expression levels of mTOR, raptor, or rictor, but, as expected (Kim, D.-H. et al. *Cell* 110, 163-175 (2002)), it strongly reduced the amounts of raptor recovered with mTOR within 30 minutes of addition to HeLa or PC3 cells (FIG. 7a). In contrast, at early time points after addition to HeLa cells, rapamycin did not reduce the amounts of rictor bound to mTOR, but after 24 hours the drug did cause a partial loss of rictor from mTOR. Rapamycin treatment had a similar but more pronounced effect in PC3 cells, with an almost complete loss of mTOR-bound rictor after 24 hours. Concentrations of rapamycin ranging from 5 nM to 1 uM produced identical effects to 100 nM on the raptor-mTOR and rictor-mTOR interactions. In addition, rapamycin treatment times of 48 and 72 hours gave identical results to 24-hour treatments in HeLa and PC3 cells (FIG. 7b).

Using a cross-linking assay Applicants previously demonstrated that the binding of FKBP12-rapamycin to mTORC1 does not break the raptor-mTOR interaction within cells but only weakens it so that it cannot survive biochemical isolation (Kim, D.-H. et al. *Cell* 110, 163-175 (2002)). A similar mechanism cannot explain the loss of the rictor-mTOR interaction in rapamycin-treated cells because FKBP12-rapamycin cannot bind to a formed mTORC2 (Sarbassov, D. D. et al. *Curr Biol* 14, 1296-302 (2004); Jacinto, E. et al. *Nat Cell Biol* 6, 1122-8 (2004)). Instead, Applicants suspected that after prolonged rapamycin treatment a large fraction of the rictor and mTOR molecules within cells are no longer associated with each other. Applicants tested this possibility in a modified version of the experiment in FIG. 7a. Applicants first treated cells with a reversible cross-linker that covalently links mTOR to associated proteins and then lysed the cells with a buffer that breaks non-covalent interactions. As expected (Sarbassov, D. D. et al. *Curr Biol* 14, 1296-302 (2004); Kim, D.-H. et al. *Cell* 110, 163-175 (2002)), in untreated cells raptor and rictor co-immunoprecipitated with mTOR only when the cross linker had been added (FIG. 7c). In cells treated with rapamycin the cross-linker preserved the interaction of raptor with mTOR but did not prevent the loss of the rictor-mTOR association caused by prolonged rapamycin treatment (FIG. 7c). These results confirm that rapamycin affects mTORC1 and mTORC2 in different ways. mTORC1 is destabilized at all times after drug addition, consistent with the capacity of FKBP12-rapamycin to bind to it and weaken the raptor-mTOR interaction (Kim, D.-H. et al. *Cell* 110, 163-175 (2002)). On the other hand, prolonged treatment of cells with rapamycin leads to a progressive loss of the rictor-mTOR interaction to an extent that varies with cell type. Prolonged incubation of cell lysates with rapamycin did not disrupt the rictor-mTOR interaction (FIG. 11), suggesting that rapamycin exerts its effects on a process that occurs within cells, such as mTORC2 assembly.

To test this Applicants pulsed-labeled HeLa and PC3 cells with $^{35}$S-methionine/cysteine in the presence or absence of rapamycin and followed the amount of newly-synthesized (i.e. $^{35}$S-labeled) mTOR bound to rictor during a chase period with unlabeled amino acids. In the absence of rapamycin and at all times during the chase period Applicants readily detected newly-synthesized mTOR bound to immunoprecipitated rictor in both HeLa and PC3 cells (FIG. 7d). Strikingly, rapamycin prevented the binding of newly-synthesized mTOR to rictor in PC3 cells and greatly reduced it in HeLa cells (FIG. 7d). Quantification of these results revealed that rapamycin prevented 100% and 80% of the interaction between newly-synthesized mTOR and rictor in PC3 and HeLa cells, respectively (FIG. 7e). Rapamycin does not inhibit mTOR or rictor protein synthesis because the drug did not reduce the amount of radiolabelled mTOR or rictor immunoprecipitated by the mTOR or rictor antibody, respectively (FIG. 7d). These results indicate that in HeLa cells a fraction of mTORC2 assembles even in the presence of rapamycin, a result consistent with the finding that some rictor remains bound to mTOR in HeLa cells grown for 72 hours in the presence of rapamycin (FIG. 7b). On the other hand, rapamycin completely blocks mTORC2 assembly in PC3 cells.

Because the interaction of mTOR with rictor is necessary for mTOR to phosphorylate S473 of Akt/PKB, Applicants asked if a 24-hour treatment with rapamycin inhibits Akt/

PKB phosphorylation. In several cell lines Applicants compared the effects of rapamycin on the phosphorylation of S473 of Akt/PKB and of T389 of S6K1, a well-known mTORC1 phosphorylation site (Burnett, P. E. et al. *PNAS* 95, 1432-1437 (1998)) (FIG. 8a). In PC3, HEK-293T, HeLa, and H460 cells 1- or 24-hour treatments with rapamycin eliminated S6K1 phosphorylation, consistent with inhibition of mTORC1. Because S6K1 normally suppresses the PI3K/Akt pathway (Tremblay, F. & Marette, A. *J Biol Chem* 276, 38052-60. (2001); Harrington, L. S. et al. *J Cell Biol* 166, 213-23 (2004); Um, S. H. et al. *Nature* 431, 200-5 (2004)), inhibition of S6K1 by rapamycin should lead to an increase in Akt/PKB phosphorylation and, indeed, this happened in HeLa and H460 cells. However, in PC3 cells the drug strongly decreased Akt/PKB phosphorylation, while, as previously reported (Edinger, A. L. et al. *Cancer Res* 63, 8451-60 (2003)), it caused a weak inhibition in HEK-293T cells. Changes in the phosphorylation of T308 of Akt/PKB paralleled those occurring on S473, as expected from the proposed role of S473 phosphorylation in regulating the phosphorylation of T308 by PDK1 (Scheid, M. P. et al. *Mol Cell Biol* 22, 6247-60 (2002); Yang, J. et al. *Mol Cell* 9, 1227-40 (2002)). This initial survey suggests that a 24-hour treatment with rapamycin can cause either (1) a strong inhibition, (2) a partial inhibition, or (3) an increase in Akt/PKB phosphorylation. To determine the frequency of these responses Applicants tested the effects of 1 and 24 hours of rapamycin treatment on Akt/PKB phosphorylation in 33 cancer or transformed cell lines (FIG. 16). In about one third of the cell lines rapamycin caused a strong or partial inhibition of Akt/PKB phosphorylation while the drug either did not affect or increased Akt/PKB phosphorylation in the others. FIG. 8b shows three representative cell lines for each type of response. Applicants also examined a variety of primary and non-transformed cell lines and found several, including endothelial and muscle cells, with rapamycin-sensitive Akt/PKB phosphorylation (FIG. 8c and FIG. 16). Lastly, Applicants showed that rapamycin can inhibit Akt/PKB phosphorylation in vivo, as mice treated daily for one week with the drug had decreased Akt/PKB phosphorylation in the thymus, adipose tissue, heart, and lungs (FIG. 12). These findings indicate that rapamycin-sensitive Akt/PKB phosphorylation is common, and occurs in cultured normal and cancer cell lines as well as in vivo. It is also clear that the sensitivity of a cell line cannot be predicted based on its tissue of origin.

Figure 7:
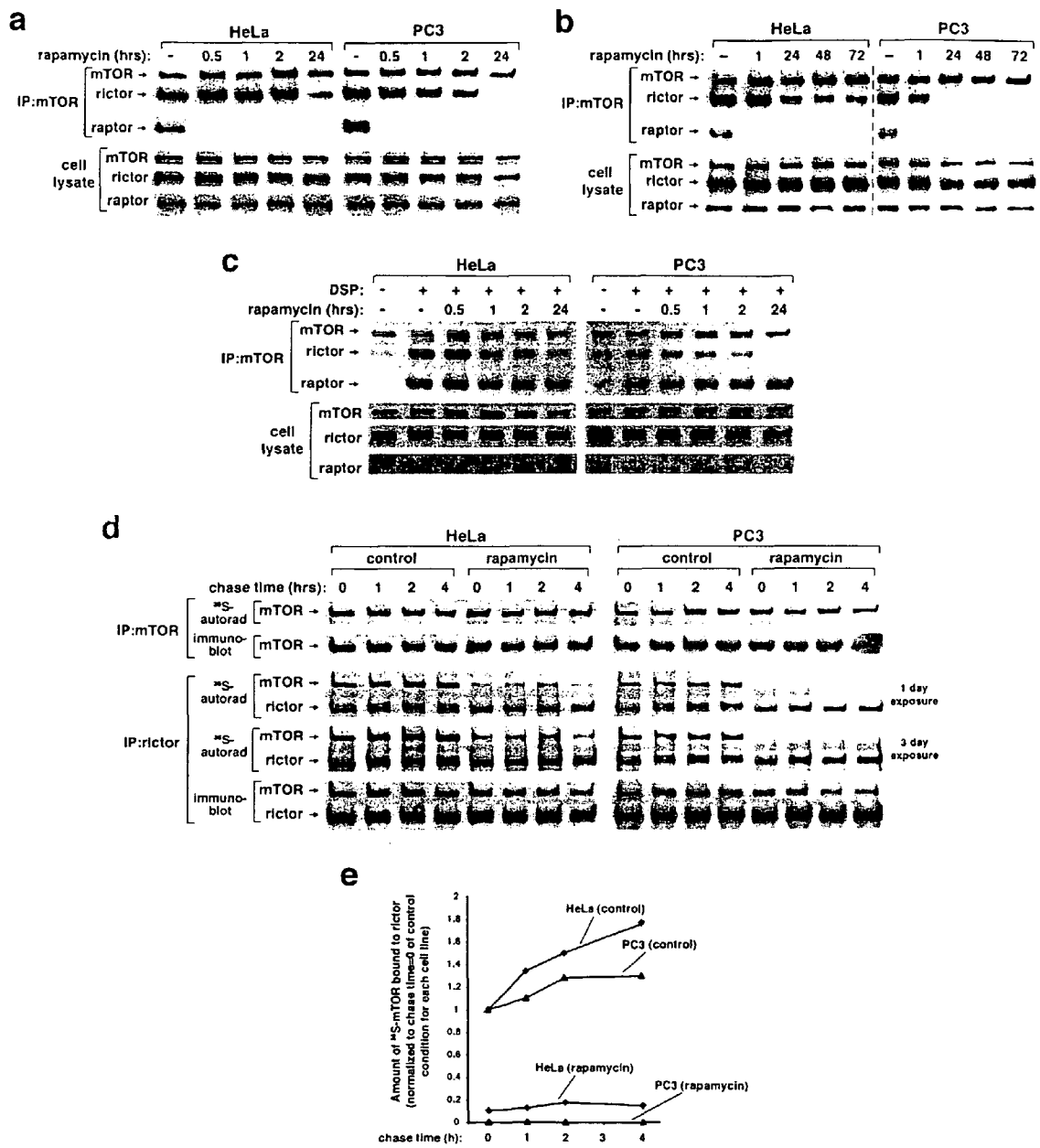
FIGS. 7A-7E show that prolonged treatment of cells with rapamycin inhibits assembly of mTORC2. (A) HeLa and PC3 cells were treated with 100 nM rapamycin for the indicated times. Cell lysates and mTOR-immunoprecipitates prepared from the lysates were analyzed by immunoblotting for the levels of mTOR, rictor and raptor. (B) HeLa and PC3 cell lines were treated with 100 nM rapamycin for 24, 48, or 72 hours, and analyzed as above. (C) In rapamycin-treated cells, use of a reversible cross-linker preserves the raptor-mTOR but not the rictor-mTOR interaction. Experiment was performed as in (A) except that where indicated cells were treated with the DSP cross-linker before lysis with a buffer containing Triton X-100. (D) Pulse-chase experiment indicates that rapamycin inhibits assembly of the mTORC2 without suppressing mTOR or rictor synthesis. Cells were pretreated with 100 nM rapamycin or vehicle control for 20 minutes and then pulsed with $^{35}$S-methionine/cysteine and chased with cold amino acids for the indicated periods of time. Rictor and mTOR immunoprecipitates were prepared from cell lysates and analyzed by autoradiography and immunoblotting for the levels of newly synthesized and total mTOR and rictor. (E) Quantification of the amount of newly synthesized mTOR bound to rictor in control or rapamycin-treated HeLa and PC3 cells.

Why does rapamycin inhibit Akt/PKB phosphorylation in only certain cell types? The experiments in FIG. 7 clearly showed that long-term rapamycin treatment does not always lead to the total loss of intact mTORC2 (FIG. 7ab) and that mTORC2 assembly is not completely blocked in all cell types (FIG. 7d). Considering this Applicants hypothesized that cell lines with rapamycin-sensitive Akt/PKB phosphorylation would have very low amounts of intact mTORC2 complexes after prolonged rapamycin treatment. Consistent with this, cell lines with rapamycin-sensitive Akt/PKB phosphorylation (PC3, BJAB, Jurkat), had less intact rictor-mTOR complexes following 1 hour of drug treatment and an almost complete loss of complexes by 24 hours (FIG. 9a). In contrast, cell lines with rapamycin-insensitive Akt/PKB phosphorylation (H460, HeLa, LNCaP, 768-0) showed stable levels of intact rictor-mTOR complexes after 1 hour of drug treatment and only a partial loss by 24 hours (FIG. 9a). The degree of loss of the complexes after rapamycin treatment correlated with their residual in vitro kinase activity towards Akt/PKB (FIG. 9b). Rictor immunoprecipitates prepared from PC3, BJAB, and Jurkat cells treated with rapamycin for 24 hours had almost background levels of kinase activity, consistent with the large loss of mTOR from these immunoprecipitates. On the other hand, in HeLa and H460 cells treated with rapamycin for 24 hours, a greater amount of mTOR remained bound to rictor and this correlated with a higher level of kinase activity towards Akt/PKB. Thus, Applicants' results suggest that in certain cell types the small amount of mTORC2 assembled in the presence of rapamycin is sufficient to mediate Akt/PKB phosphorylation.

To test this hypothesis Applicants asked if it is possible to confer rapamycin-sensitive Akt/PKB phosphorylation to a cell line by partially decreasing the expression of mTOR. A reduction in total mTOR should decrease the levels of mTORC2 in the cells so that rapamycin-mediated suppression of mTORC2 assembly will leave insufficient amounts of mTORC2 to mediate Akt/PKB phosphorylation. This is exactly what Applicants observe. A partial knockdown of mTOR in HEK-293T, HeLa, and H460 cells is sufficient to render Akt/PKB phosphorylation rapamycin-sensitive in these cell lines (FIG. 9c). Strikingly, in HeLa and H460 cells a partial knockdown of mTOR induced a strong increase in Akt/PKB phosphorylation—a finding consistent with removal of the inhibitory signal coming from S6K1—and this increase was suppressed by rapamycin. That low amounts of mTORC2 are sufficient to mediate phosphorylation of S473 of Akt/PKB is consistent with the finding that only 10% of normal PDK1 levels are needed for the full phosphorylation of T308 of Akt/PKB (Lawlor, M. A. et al. *Embo J* 21, 3728-38. (2002)).

Figure 10:
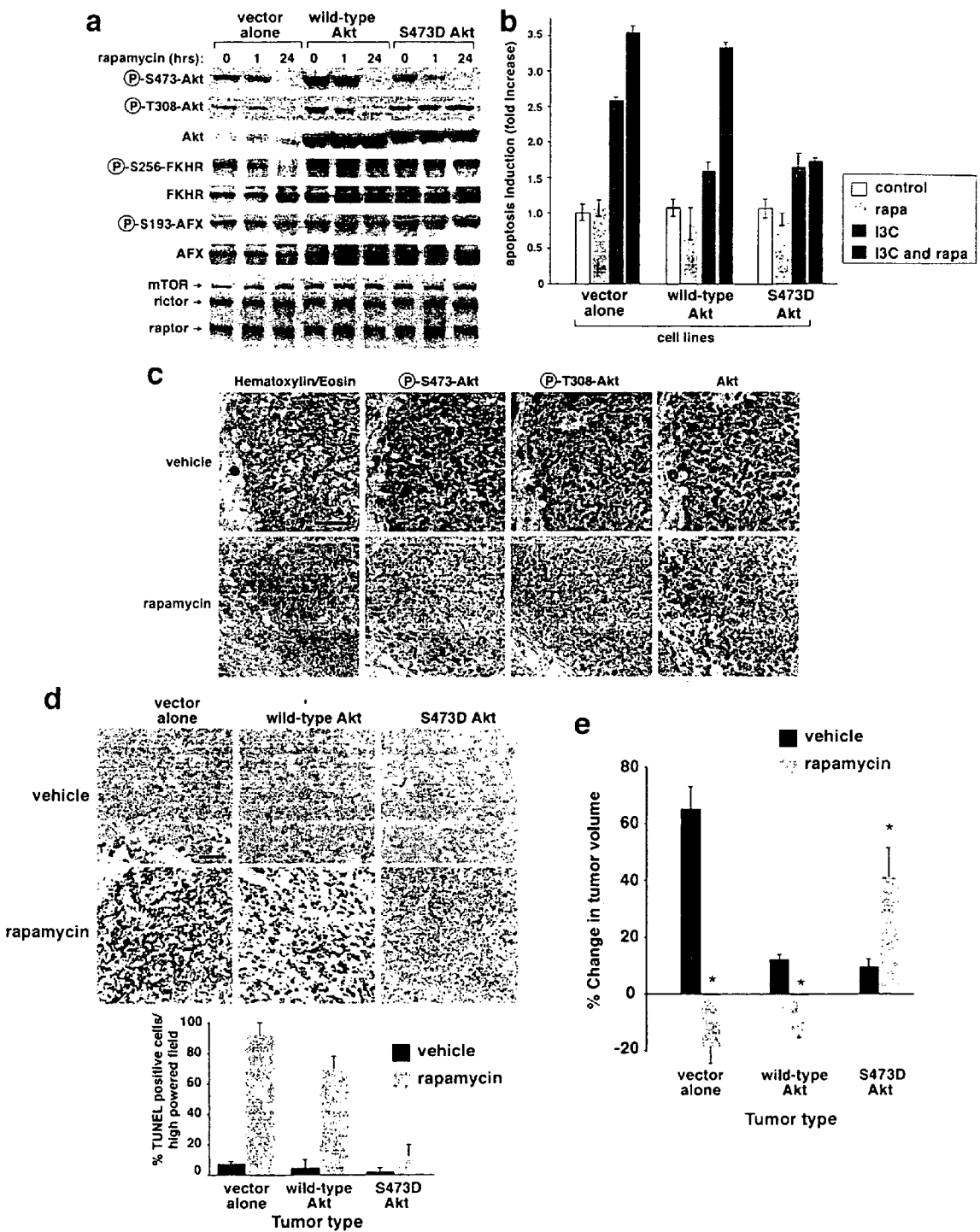

Because S473 phosphorylation is required for full Akt/PKB activation (reviewed in Scheid, M. P. & Woodgett, J. R. *FEBS Lett* 546, 108-12 (2003)), Applicants expected that inhibition of S473 phosphorylation by rapamycin to suppress Akt/PKB signaling. In PC3 cells rapamycin inhibited the phosphorylation of FKHR (Foxo1) and AFX (Foxo4a) (FIG. 10a), forkhead family transcription factors that are direct substrates of Akt/PKB (Brunet, A. et al. *Cell* 96, 857-68 (1999); del Peso, L., et al. *Oncogene* 18, 7328-33 (1999); Kops, G. J. et al. *Nature* 398, 630-4 (1999); Rena, G. et al. *Embo J* 21, 2263-71 (2002); Takaishi, H. et al. *Proc Natl Acad Sci USA* 96, 11836-41 (1999); Tang, E. D. et al. *J Biol Chem* 274, 16741-6 (1999)). Expression of either the phospho-mimetic S473D mutant of Akt1/PKB1 or wild-type Akt1/PKB 1 increased the phosphorylation of FKHR and AFX (FIG. 10a). However, only expression of S473D Akt1/PKB1 prevented the inhibition of FKHR, AFX, and T308 Akt1/PKB1 phosphorylation caused by rapamycin (FIG. 10a). The capacity of the S473D mutant to prevent the effects of rapamycin indicates that rapamycin-mediated inhibition of S473 phosphorylation leads to the decrease in the phosphorylation of FKHR, AFX, and T308 Akt/PKB. Because Akt/PKB has a well-known pro-survival role Applicants asked if rapamycin could potentiate a cell death signal as well as prevent the capacity of Akt/PKB to suppress apoptosis. Indeed, treatment of PC3 cells with rapamycin and submaximal concentrations of indole-3-carbinol, a small molecule known to induce apoptosis in PC3 cells (Chinni, S. R.& Sarkar, F. H. *Clin Cancer Res* 8, 1228-36 (2002)), showed greater levels of apoptosis than treatment with indole-3-carbinol alone (FIG. 10b). The expression of either wild-type or S473D Akt1/PKB1 decreased the capacity of indole-3-carbinol to induce apoptosis. However, the addition of rapamycin strongly reduced the pro-survival effect conferred by wild-type Akt1/PKB1 but not by the S473D mutant.

Rapamycin had analogous effects in tumor xenografts made from these cell lines in immunocompromised mice. In tumors derived from vector alone PC3 cells rapamycin strongly decreased the phosphorylations of S473 and T308 of Akt/PKB without affecting Akt/PKB expression (FIG. 10c). The drug also caused a sharp increase in the number of cells undergoing apoptosis within the tumor and this effect was strongly suppressed by the expression of the S473D Akt1/PKB1 mutant but only partially by wild type Akt1/PKB1 (FIG. 10d). In addition, expression of the S473D mutant but not wild type Akt1/PKB1 suppressed the capacity of rapamycin to decrease tumor volume (FIG. 10e). Rapamycin-mediated inhibition of mTORC1 is known to sensitize cells to pro-apoptotic stimuli in certain cell lines. Applicants' data indicate that inhibition of mTORC2 by rapamycin contributes to the pro-apoptotic effects of rapamycin.

Figure 15:
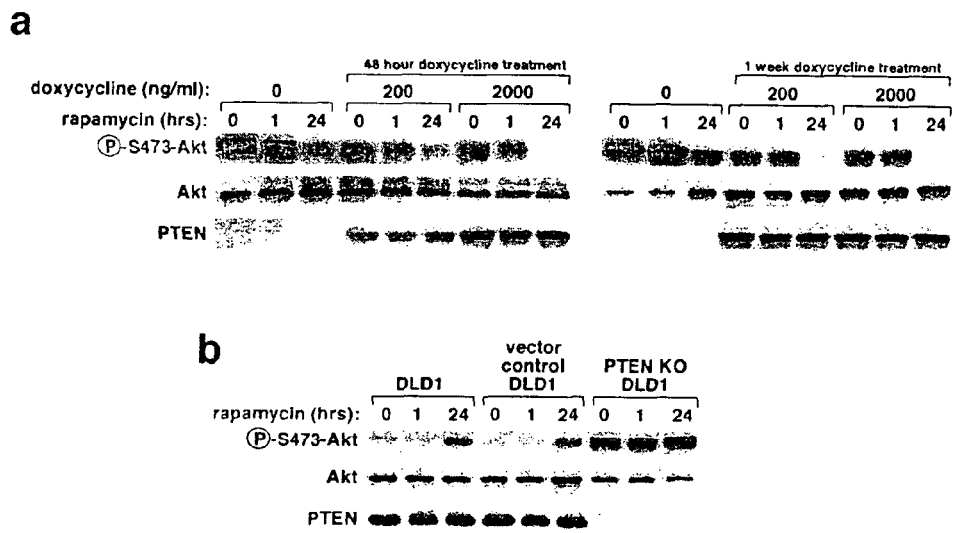

Applicants' findings may be of value for determining which cancers or other diseases should be treated with rapamycin or its analogues (CCI 779, RAD001, AP23573). It will be important to identify biomarkers that can predict if Akt/PKB is sensitive to rapamycin in a particular cell type and to design dosing regimens that ensure Akt/PKB inhibition. Applicants suspect that Applicants' existing predictive test—the amount of rictor-mTOR complex remaining after rapamycin treatment—will be difficult to perform in a clinical setting. To obtain a biomarker it will be necessary to understand why in certain cell lines (e.g., HeLa) a significant fraction of mTORC2 is able to assemble even in the presence of rapamycin while in other cell lines this does not happen. A possible mechanism is that in certain cell types a fraction of the mTORC2s assembles in such a way that the FKBP12-rapamycin binding site is never accessible to the drug, perhaps because an unidentified protein or post-translational modification blocks the binding site. Applicants' preliminary analyses have failed to find a strong correlation between the rapamycin-sensitivity of Akt/PKB phosphorylation in a cell line and the expression levels of rictor, mTOR, raptor, Akt/PKB, S6K1, or FKBP12; the rates of cell proliferation in culture; the concentration of rapamycin used; or the tissue of origin. In addition, the forced overexpression of FKBP12 does not affect the rapamycin sensitivity of Akt/PKB phosphorylation (FIG. 13) and the half-lives of mTOR or rictor protein are not significantly different between sensitive and insensitive cell lines (FIG. 14). Applicants have noticed that many of the cancer cell lines with rapamycin-sensitive Akt/PKB phosphorylation are also null for PTEN (FIG. 16). However, deletion of PTEN in the PTEN-positive DLD1 colon cancer line or expression of PTEN in the PTEN-null Jurkat T-cell leukemia line failed to confer or eliminate, respectively, sensitivity to rapamycin of Akt/PKB phosphorylation (FIG. 15). Thus, PTEN loss is neither necessary nor sufficient for obtaining rapamycin-sensitive Akt/PKB phosphorylation.

Applicants' work indicates that rapamycin inhibits Akt/PKB signaling in cells where the drug decreases the levels of intact mTORC2 below those needed to maintain the phosphorylation of S473 of Akt/PKB. Applicants suggest that rapamycin is a cell-type dependent inhibitor of mTORC2 function as well as a universal inhibitor of the mTORC1 pathway. Rapamycin is in clinical trials as a treatment for cancer and has established uses in preventing vascular restenosis and the immune rejection of transplanted organs. It is interesting to note that Akt/PKB has important roles in the pathological processes implicated in all these conditions. A high fraction of tumors have activated Akt/PKB signaling as a result of PTEN loss and these cancers may be particularly sensitive to rapamycin (reviewed in Guertin, D. A. & Sabatini, D. M. *Trends Mol Med* 11, 353-61 (2005)). Rapamycin is known to have anti-angiogenic effects (Guba, M. et al. *Nat Med* 8, 128-35 (2002)) and Applicants find that the drug strongly inhibits Akt/PKB in endothelial cells (FIG. 8c). Akt/PKB plays key roles in T-lymphocytes (reviewed in Kane, L. P. & Weiss, A. *Immunol Rev* 192, 7-20 (2003)) and smooth muscle cells (reviewed in Zhou, R. H. et al. *Arterioscler Thromb Vasc Biol* 23, 2015-20 (2003)), the cellular targets of rapamycin in its immunosuppressive and anti-restenotic uses, respectively. In addition, rapamycin-mediated inhibition of Akt/PKB may help explain the side effects of the drug. For example, rapamycin strongly inhibits Akt/PKB phosphorylation in adipose tissue (FIG. 12), a tissue type where insulin-stimulated Akt/PKB activity plays an important role in suppressing lipolysis (Elks, M. L. & Manganiello, V. C. *Endocrinology* 116, 2119-21 (1985); Wijkander, J. et al. *Endocrinology* 139, 219-27 (1998)). Inhibition of Akt/PKB by rapamycin in adipocytes may allow lipolysis to remain high even in the presence of insulin, resulting in the accumulation of free fatty acids in the plasma that can be used by the liver to generate triglycerides. This series of events may provide a molecular mechanism for the hyperlipidemia commonly seen in patients treated with rapamycin (Morrisett, J. D. et al. *Transplant Proc* 35, 143S-150S (2003)). Thus, Applicants propose that rapamycin-mediated inhibition of mTORC2 contributes to the clinical effects of the drug.

Materials and Methods

1. Materials

Reagents were obtained from the following sources: protein G-sepharose and Dithiobis[succinimidyl propionate] (DSP) from Pierce; rapamycin from Calbiochem; DMEM, RPMI, F12, and MCDB 131 from Life Technologies; Fetal Bovine Serum (FBS), Heat Inactivated Fetal Bovine Serum (IFS), and indole-3-carbinol (I3C) from Sigma; EGM-2 media from Cambrex; antibodies to mTOR, S6K1, and ATM as well as HRP-labeled anti-mouse, anti-goat, and anti-rabbit secondary antibodies from Santa Cruz Biotechnology; and antibodies to phospho-T389 S6K1, phospho-S6, phospho-S473 and phospho-T308 Akt/PKB, Akt/PKB (all three Akt/PKB-directed antibodies recognize the three known Akt/PKB isoforms), phospho-S256 FKHR (also recognizes phospho-S193 of AFX), and AFX from Cell Signaling Technologies. Antibodies to rictor and raptor were previously described (Sarbassov, D. D. et al. *Curr Biol* 14, 1296-302 (2004)).

2. Cell Lines.

Cell lines were cultured in the following media: Jurkat, BJAB, SKW3, U937, Ishikawa, HepG2, A375, A549, and H460 cells in RPMI with 10% IFS; OPM2, Δ47, LNCaP, UACC-903, Kym-1, Rd88SC.10, rh30, and rSMC cells in RMPI with 10% FBS; PC3, HeLa, HeLa S3, U2OS, Mel-STR, u87, 786-0, HEK-293T, MD-MBA-231, MD-MBA-468, HT29, c2c12 and MEFs (p53−/−) cells in DMEM with 10% IFS; CACO2, 827, and SW480 cells in DMEM with 10% FBS; BJ fibroblasts in DMEM/F12 with 10% IFS; HUVECs in MCDB 131 media supplemented with EGM-2 and 5% FBS; and HMLE cells in 1:1 DMEM/F12 supplemented with insulin, epidermal growth factor (EGF), and hydrocortisone. All the above cell lines were cultured at a density that allowed cell division throughout the course of the experiment. 3T3-L1 cells were cultured and differentiated as described (Frost, S. C. & Lane, M. D. *J Biol Chem* 260, 2646-52 (1985)). Parental, vector control, and PTEN-null DLD1 cells were cultured as described (Lee, C. et al. *Cancer Res* 64, 6906-14 (2004)) as were Jurkat cells having a doxycycline-inducible PTEN (Xu, Z. et al. *Cell Growth Differ* 13, 285-96 (2002)).

3. Rapamycin-Treatment of Mice and Organ Harvest.

1 mg of rapamycin was dissolved in 20 μl of ethanol, which was then diluted with Ringer's saline solution to a final concentration of 1 mg/ml directly before use. Three-month old male C57BL/6NTac (Taconic) mice were administered daily intraperitoneal injections of 10 mg/kg rapamycin or the drug vehicle for 7 days. Mice were then euthanized with $CO_2$, organs were harvested into RIPA buffer, and homogenized with mechanical disruption followed by sonication. Lysates from vehicle- and rapamycin-treated organ pairs were normalized for protein content and analyzed by immunoblotting as described (Kim, D.-H. et al. *Cell* 110, 163-175 (2002)). The vehicle- and rapamycin-treated mice ate similar amounts during the 7-day treatment period and at necropsy all mice had evidence of processed food in their stomachs and small intestines. Control experiments using phospho-S6 as a marker of the effectiveness of rapamycin reveals that the drug penetrates all major tissues except the brain. The experiment was repeated twice with similar results.

4. Cell Lysis, Immunoblotting, and Cross-Linking Assay.

Cells growing in 10 cm diameter dishes were rinsed once with cold PBS and lysed on ice for 20 min in 1 ml of ice-cold Buffer A (40 mM Hepes pH 7.5, 120 mM NaCl, 1 mM EDTA, 10 mM pyrophosphate, 10 mM glycerophosphate, 50 mM NaF, 0.5 mM orthovanadate, and EDTA-free protease inhibitors (Roche)) containing 1% Triton X-100. After clearing of the lysates by centrifugation at 13,000× g for 10 min, samples containing 50-100 µg of protein were resolved by SDS-PAGE and proteins transferred to PVDF and visualized by immunoblotting as described (Kim, D.-H. et al. *Cell* 110, 163-175 (2002)). For experiments with FKHR and AFX the Triton X-100 insoluble materials were solubilized in 1% SDS in 10 mM Tris-HCl pH 7.4 by heating at 100° C. for 3 minutes followed by a brief sonication. Equal protein amounts were then analyzed by immunoblotting. For standard immunoprecipitation experiments the cell lysis buffer consisted of Buffer A containing 0.3% CHAPS instead of 1% Triton X-100 in order to preserve the integrity of the mTOR complexes (Sarbassov, D. D. et al. *Curr Biol* 14, 1296-302 (2004); Kim, D.-H. et al. *Cell* 110, 163-175 (2002)). When used, DSP was prepared as a stock solution of 50 mg in 200 µl of DMSO and added to a final concentration in the cell culture medium of 1 mg/ml (2.5 mM) (Sarbassov, D. D. et al. *Curr Biol* 14, 1296-302 (2004); Kim, D.-H. et al. *Cell* 110, 163-175 (2002)). Cells were then incubated at 37° C., 5% $CO_2$ and after 10 minutes the DSP was quenched by adding Tris-HCL, pH 8.0 to a final concentration of 100 mM. After a further 10 minute incubation at 37° C., 5% $CO_2$ cells were lysed in Buffer A containing Triton X-100. On occasion DSP used at these high concentrations can form a precipitate but this has no effect on the performance of the cross-linking assay. Reducing conditions were used during the SDS-PAGE analysis of immunoprecipitates prepared from DSP-treated cells to ensure breaking of the cross-linking disulfide bonds.

5. Immunoprecipitations and Kinase Assays.

To the cleared lysates prepared as above 4 µg of mTOR, rictor, or ATM antibodies was added per 1.2 mg of soluble protein and immune complexes were allowed to form by incubating with rotation for 90 minutes at 4° C. 25 µl of a 50% slurry of protein G-sepharose was then added and the incubation continued for 1 h. Immunoprecipitates captured with protein G-sepharose were washed four times with CHAPS-containing Buffer A and analyzed by immunoblotting as described (Sarbassov, D. D. et al. *Curr Biol* 14, 1296-302 (2004)). Immunoprecipitates used in kinase assays were also washed once with the rictor-mTOR kinase buffer (25 mM Hepes pH 7.5, 100 mM potassium acetate, 1 mM $MgCl_2$). In kinase reactions immunoprecipitates were incubated in a final volume of 15 µl for 20 min at 37° C. in the rictor-mTOR kinase buffer containing 500 ng inactive Akt1/PKB1 (Akt1/PKB1, Upstate Biotechnology, #14-279) and 500 µM ATP. The reaction was stopped by the addition of 200 µL ice-cold Enzyme Dilution buffer (20 mM MOPS, pH 7.0, 1 mM EDTA, 0.01% Brij 35, 5% glycerol, 0.1% 2-mercaptoethanol, 1 mg/ml BSA). After a quick spin, the supernatant was removed from the protein G-sepharose and a 20 µl portion was analyzed by immunoblotting (Kim, D.-H. et al. *Cell* 110, 163-175 (2002)).

6. $^{35}$S-Labeling and Pulse-Chase Experiments.

$4\times10^6$ Hela or PC3 cells growing in 100 mm dishes were treated with 100 nM rapamycin or vehicle control for 20 minutes, rinsed once in methionine- and cysteine-free DMEM, and then incubated in 3.5 ml of the same medium containing 10% dialyzed serum and 0.1 mCi/ml of $^{35}$S-methionine/$^{35}$S-cysteine (Express Protein Labeling Mix, Perkin Elmer). After allowing the cells to label for 30 minutes, the cells were washed once in the normal culture medium and incubated in fresh medium for the periods of time indicated in the figures. Cells were then lysed in CHAPS lysis buffer and rictor and mTOR immunoprecipitates prepared as described above. Quantification was performed using images acquired with a phosphoimager.

7. Lentiviral shRNA Cloning, Production, and Infection.

Lentiviral shRNAs were generated and used as described (Sarbassov, D. D. et al. *Science* 307, 1098-101 (2005)).

8. Apoptosis Induction and Detection.

Cell lines stably expressing wild-type or S473D human Akt1/PKB1 were generated by infecting PC3 cells with retroviruses made from the MSCV vector system (Clontech). cDNAs were cloned into pMSCV-hygro at the Xho1/EcoR1 site and retroviruses were generated as described (Ali, S. M. & Sabatini, D. M. *J Biol Chem* 280, 19445-8 (2005)). Cells were selected for one week in 200 µg/ml hygromycin before use. 15,000 PC3 (MSCV controls, WT Akt1/PKB1, or 473D Akt1/PKB1) cells were seeded in the wells of a 96 well-plate and cultured overnight. The next day the cells were rinsed once in serum-free medium and then cultured for 48 hrs in serum-free medium containing either DMSO (the small molecule vehicle), 100 nM rapamycin, 100 µM indole-3-carbinol, or both rapamycin and indole-3-carbinol. When indole-3-carbinol was used, 0.002% BSA was added to the medium. After 48 hours in culture all cells (adherent and floating) were processed with the Cell Death Detection Elisa plus (Roche, cat# 1774425) as described by the manufacturer.

9. Tumor Xenografts, Immunohistochemistry, and In Situ Apoptosis Assays.

PC3 cell lines stably expressing wild-type or S473D human Akt1/PKB1 or the empty vector were xenografted into six-week old immunodeficient mice (Ncr nu/nu mice; Taconic). All animal studies were performed according to the official guidelines from the MIT Committee on Animal Care and the American Association of Laboratory Animal Care. $3\times10^6$ PC3 cells were injected subcutaneously in the upper flank region of mice that had been anaesthetized with isoflurane. Tumors were allowed to grow to at least 50 mm³ in size and then treated with rapamycin (10 mg/kg) for two days. Mice were then sacrificed, the tumors excised, and tumor volumes estimated with the formula: volume=$(a^2\times b)/2$, where a=short and b=long tumor lengths, respectively, in millimeters. Sections of paraffin-embedded tumors on slides were processed for immunohistochemistry using the following primary antibodies and dilutions: 1:50 Akt1 (2H10, Cell Signaling Technology), 1:50 phospho-S473 Akt (736E11, Cell Signaling Technology), and 1:100 phospho-T308 Akt (244F9, Cell Signaling Technology). Briefly, sections were dewaxed and incubated in 3% $H_2O_2$ for 10 min at room temperature to quench endogeneous peroxidases and then processed for antigen retrieval by incubating in 10 mM sodium citrate buffer (pH 6) for 10 min in a sub-boiling water bath in a microwave oven. The sections were then incubated in blocking solution (5% horse serum in 1×TBST buffer) for 30 min at room temperature, washed three times, and then incubated overnight at 4° C. with primary antibody diluted in blocking solution. The next day, sections were incubated with the biotinylated secondary antibody for 1 hr at room temperature, washed three times, incubated 30 minutes with streptavidin-HRP (DakoCytomation), rewashed, and developed with DAB reagents (DakoCytomation) for 5-20 min until staining appeared. The slides were counterstained with hematoxylin, dehydrated, and mounted with coverslips. All washes were for 5 min in 1×TBST wash buffer (1×TBS with 0.1% Tween 20). An in situ cell death detection kit (Roche) was used as described by the manufacturer to detect apoptotic cells in tumors. Percentages of apoptotic cells per high-power field were quantified in a blinded fashion.

INCORPORATION BY REFERENCE

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of identifying an agent that inhibits mammalian Akt kinase activity, comprising:
   a) contacting a test agent with mammalian Akt polypeptide and an isolated or purified mammalian rictor-mTOR complex under conditions appropriate for phosphorylation of Akt by the rictor-mTOR complex; and
   b) assaying for phosphorylation of Akt by the rictor-mTOR complex that occurs in the presence of the test agent, as compared to phosphorylation of Akt by the rictor-mTOR complex that occurs in the absence of test agent, wherein the test agent is an agent that inhibits mammalian Akt kinase activity if the test agent decreases phosphorylation of Akt by the rictor-mTOR complex.

2. The method of claim 1, wherein the method comprises testing a library of test agents.

3. The method of claim 1, wherein the isolated or purified rictor-mTOR complex is a recombinant complex.

4. The method of claim 1, wherein the phosphorylation of Akt is on S473.

5. The method of claim 1, wherein the test agent is a small organic molecule.

6. The method of any one of claims 1 and 2-5, wherein the mammalian Akt polypeptide and the mammalian rictor-mTOR complex are human.

* * * * *

SEQUENCE LISTING

```
<160> NUMBER OF SEQ ID NOS: 16

<210> SEQ ID NO 1
<211> LENGTH: 52
<212> TYPE: DNA
<213> ORGANISM: Unknown
<220> FEATURE:
<223> OTHER INFORMATION: oligonucleotide primer

<400> SEQUENCE: 1
gaattaatac gactcactat agggagatta agctattgga agagaatcat gc         52

<210> SEQ ID NO 2
<211> LENGTH: 52
<212> TYPE: DNA
<213> ORGANISM: Unknown
<220> FEATURE:
<223> OTHER INFORMATION: oligonucleotide primer

<400> SEQUENCE: 2
gaattaatac gactcactat agggagaatc gatttctgat ttgcttaaag tg         52

<210> SEQ ID NO 3
<211> LENGTH: 51
<212> TYPE: DNA
<213> ORGANISM: Unknown
<220> FEATURE:
<223> OTHER INFORMATION: oligonucleotide primer

<400> SEQUENCE: 3
gaattaatac gactcactat agggagagtc aataaacaca actttcgacc t          51

<210> SEQ ID NO 4
<211> LENGTH: 52
<212> TYPE: DNA
<213> ORGANISM: Unknown
<220> FEATURE:
<223> OTHER INFORMATION: oligonucleotide primer

<400> SEQUENCE: 4
gaattaatac gactcactat agggagagaa tatttgagtg aaatgaggaa cg         52

<210> SEQ ID NO 5
<211> LENGTH: 62
<212> TYPE: DNA
<213> ORGANISM: Unknown
<220> FEATURE:
<223> OTHER INFORMATION: oligonucleotide primer
```

-continued

```
<400> SEQUENCE: 5
ccggccgcat tgtctctatc aagttcttcc tgtcaaactt gatagagaca atgcggtttt    60
tg                                                                  62

<210> SEQ ID NO 6
<211> LENGTH: 62
<212> TYPE: DNA
<213> ORGANISM: Unknown
<220> FEATURE:
<223> OTHER INFORMATION: oligonucleotide primer

<400> SEQUENCE: 6
aattcaaaaa ccgcattgtc tctatcaagt ttgacaggaa gaacttgata gagacaatgc    60
gg                                                                  62

<210> SEQ ID NO 7
<211> LENGTH: 62
<212> TYPE: DNA
<213> ORGANISM: Unknown
<220> FEATURE:
<223> OTHER INFORMATION: oligonucleotide primer

<400> SEQUENCE: 7
ccggggctag tctgtttcga aatttcttcc tgtcaaaatt tcgaaacaga ctagccttt     60 tg                                                                  62

<210> SEQ ID NO 8
<211> LENGTH: 62
<212> TYPE: DNA
<213> ORGANISM: Unknown
<220> FEATURE:
<223> OTHER INFORMATION: oligonucleotide primer

<400> SEQUENCE: 8
aattcaaaaa ggctagtctg tttcgaaatt ttgacaggaa gaaatttcga aacagactag    60
cc                                                                  62

<210> SEQ ID NO 9
<211> LENGTH: 57
<212> TYPE: DNA
<213> ORGANISM: Unknown
<220> FEATURE:
<223> OTHER INFORMATION: oligonucleotide primer

<400> SEQUENCE: 9
cgggcagcct tgaactgttt aacttcctgt cattaaacag ttcaaggctg cttttttg      57

<210> SEQ ID NO 10
<211> LENGTH: 58
<212> TYPE: DNA
<213> ORGANISM: Unknown
<220> FEATURE:
<223> OTHER INFORMATION: oligonucleotide primer

<400> SEQUENCE: 10
aattcaaaaa gcagccttga actgtttaat gacaggaagt taaacagttc aaggctgc      58

<210> SEQ ID NO 11
<211> LENGTH: 59
<212> TYPE: DNA
<213> ORGANISM: Unknown
<220> FEATURE:
<223> OTHER INFORMATION: oligonucleotide primer
```

```
<400> SEQUENCE: 11
ccggttcagc gtccctacct tcttctctcg agagaagaag gtagggacgc tgattttg        59

<210> SEQ ID NO 12
<211> LENGTH: 59
<212> TYPE: DNA
<213> ORGANISM: Unknown
<220> FEATURE:
<223> OTHER INFORMATION: oligonucleotide primer

<400> SEQUENCE: 12
aattcaaaaa tcagcgtccc taccttcttc tctcgagaga agaaggtagg gacgctgaa        59

<210> SEQ ID NO 13
<211> LENGTH: 58
<212> TYPE: DNA
<213> ORGANISM: Unknown
<220> FEATURE:
<223> OTHER INFORMATION: oligonucleotide primer

<400> SEQUENCE: 13
ccggagggcc ctgctactcg cttttctcga gaaaagcgag tagcagggcc cttttttg         58

<210> SEQ ID NO 14
<211> LENGTH: 57
<212> TYPE: DNA
<213> ORGANISM: Unknown
<220> FEATURE:
<223> OTHER INFORMATION: oligonucleotide primer

<400> SEQUENCE: 14
aattcaaaaa agggccctgc tactcgcttt tctcgagaaa agcgagtagc agggccc          57

<210> SEQ ID NO 15
<211> LENGTH: 59
<212> TYPE: DNA
<213> ORGANISM: Unknown
<220> FEATURE:
<223> OTHER INFORMATION: oligonucleotide primer

<400> SEQUENCE: 15
ccggtacttg tgaagaatcg tatcttctcg agaagatacg attcttcaca agttttttg        59

<210> SEQ ID NO 16
<211> LENGTH: 59
<212> TYPE: DNA
<213> ORGANISM: Unknown
<220> FEATURE:
<223> OTHER INFORMATION: oligonucleotide primer

<400> SEQUENCE: 16
aattcaaaaa acttgtgaag aatcgtatct tctcgagaag atacgattct tcacaagta       59
```